(12) United States Patent
Chuang et al.

(10) Patent No.: US 10,197,501 B2
(45) Date of Patent: Feb. 5, 2019

(54) ELECTRON-BOMBARDED CHARGE-COUPLED DEVICE AND INSPECTION SYSTEMS USING EBCCD DETECTORS

(71) Applicant: KLA-Tencor Corporation, Milpitas, CA (US)

(72) Inventors: Yung-Ho Alex Chuang, Cupertino, CA (US); Xuefeng Liu, San Jose, CA (US); John Fielden, Los Altos, CA (US); David L. Brown, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 268 days.

(21) Appl. No.: 13/710,315

(22) Filed: Dec. 10, 2012

(65) Prior Publication Data
US 2013/0148112 A1    Jun. 13, 2013

Related U.S. Application Data

(60) Provisional application No. 61/569,611, filed on Dec. 12, 2011.

(51) Int. Cl.
*G01N 21/88* (2006.01)
*H01L 27/148* (2006.01)
(Continued)

(52) U.S. Cl.
CPC ......... *G01N 21/88* (2013.01); *G01N 21/9501* (2013.01); *H01J 31/26* (2013.01);
(Continued)

(58) Field of Classification Search
CPC .. H01J 40/06; H01J 43/00; H01J 43/04; H01J 43/08; G01J 2001/4453
(Continued)

(56) References Cited

U.S. PATENT DOCUMENTS

| 3,755,704 A | 8/1973 | Spindt et al. |
| 3,870,917 A | 3/1975 | Cuny |

(Continued)

FOREIGN PATENT DOCUMENTS

| EP | 0746871 B1 | 5/2000 |
| EP | 0602983 B1 | 6/2000 |

(Continued)

OTHER PUBLICATIONS

International Search Report and Written Opinion dated Mar. 31, 2014 for PCT/US2013/074124, filed Dec. 10, 2013 in the name of KLA-Tencor Corporation.

(Continued)

*Primary Examiner* — Georgia Y Epps
*Assistant Examiner* — Don Williams
(74) *Attorney, Agent, or Firm* — Bever, Hoffman & Harms, LLP

(57) ABSTRACT

A focusing EBCCD includes a control device positioned between a photocathode and a CCD. The control device has a plurality of holes therein, wherein the plurality of holes are formed perpendicular to a surface of the photocathode, and wherein a pattern of the plurality of holes is aligned with a pattern of pixels in the CCD. Each hole is surrounded by at least one first electrode, which is formed on a surface of the control device facing the photocathode. The control device may include a plurality of ridges between the holes. The control device may be separated from the photocathode by approximately half a shorter dimension of a CCD pixel or less. A plurality of first electrodes may be provided, wherein each first electrode surrounds a given hole and is separated from the given hole by a gap.

23 Claims, 19 Drawing Sheets

(51) Int. Cl.
*G01N 21/95* (2006.01)
*H01J 31/26* (2006.01)
*G01N 21/956* (2006.01)

(52) U.S. Cl.
CPC .. *H01L 27/14806* (2013.01); *H01L 27/14818* (2013.01); *G01N 2021/8822* (2013.01); *G01N 2021/95676* (2013.01); *H01L 27/14856* (2013.01)

(58) Field of Classification Search
USPC ............... 250/207, 214 VT, 208.1; 257/77; 313/103, 105
See application file for complete search history.

(56) References Cited

U.S. PATENT DOCUMENTS

| | | | |
|---|---|---|---|
| 3,947,707 A | 3/1976 | Shannon | |
| 4,099,198 A | 7/1978 | Howorth et al. | |
| 4,210,922 A | 7/1980 | Shannon | |
| 4,275,326 A | 6/1981 | Houtkamp | |
| 4,348,690 A | 9/1982 | Jastrzebski | |
| 4,467,189 A * | 8/1984 | Tsuchiya | H01J 31/502 250/214 VT |
| 4,555,731 A * | 11/1985 | Zinchuk | H04N 5/2253 250/214 LA |
| 4,644,221 A | 2/1987 | Gutierrez et al. | |
| 4,760,031 A | 7/1988 | Janesick | |
| 4,853,595 A | 8/1989 | Alfano et al. | |
| 5,054,683 A | 10/1991 | Haisma et al. | |
| 5,120,949 A | 6/1992 | Tomasetti | |
| 5,227,313 A | 7/1993 | Gluck et al. | |
| 5,315,126 A | 5/1994 | Field | |
| 5,376,810 A | 12/1994 | Hoenk et al. | |
| 5,428,392 A | 6/1995 | Castro et al. | |
| 5,495,141 A * | 2/1996 | Thomas | H01J 29/06 313/524 |
| 55,673,702 | 10/1996 | Emery et al. | |
| 5,717,518 A | 2/1998 | Shafer et al. | |
| 5,719,069 A | 2/1998 | Sparks | |
| 5,731,584 A | 3/1998 | Beyne | |
| 5,742,626 A | 4/1998 | Mead et al. | |
| 5,760,809 A | 6/1998 | Malhotra et al. | |
| 5,760,899 A | 6/1998 | Eismann | |
| 5,852,322 A | 12/1998 | Speckbacher | |
| 5,940,685 A | 8/1999 | Loomis et al. | |
| 5,999,310 A | 12/1999 | Shafer et al. | |
| 6,013,399 A | 1/2000 | Nguyen | |
| 6,064,759 A | 5/2000 | Buckley et al. | |
| 6,162,707 A | 12/2000 | Dinh | |
| 6,201,601 B1 | 3/2001 | Vaez-Iravani et al. | |
| 6,271,916 B1 | 8/2001 | Marxer et al. | |
| 6,278,119 B1 | 8/2001 | Nikzad et al. | |
| 6,285,018 B1 * | 9/2001 | Aebi et al. | 250/214.1 |
| 6,297,879 B1 | 10/2001 | Yang et al. | |
| 6,307,586 B1 | 10/2001 | Costello | |
| 6,362,484 B1 | 3/2002 | Beyne | |
| 6,373,869 B1 | 4/2002 | Jacob | |
| 6,403,963 B1 | 6/2002 | Nikzad | |
| 6,535,531 B1 | 3/2003 | Smith et al. | |
| 6,545,281 B1 | 4/2003 | McGregor | |
| 6,711,283 B1 | 3/2004 | Soenksen | |
| 6,837,766 B2 | 1/2005 | Costello | |
| 7,005,637 B2 | 2/2006 | Costello et al. | |
| 7,039,157 B2 * | 5/2006 | Fujii et al. | 378/43 |
| 7,126,699 B1 | 10/2006 | Wihl et al. | |
| 7,130,039 B2 | 10/2006 | Vaez-Iravani et al. | |
| 7,136,159 B2 | 11/2006 | Tsai et al. | |
| 7,283,166 B1 | 10/2007 | Billman | |
| 7,313,155 B1 | 12/2007 | Mu | |
| 7,321,468 B2 | 1/2008 | Herkommer et al. | |
| 7,345,825 B2 | 3/2008 | Chuang et al. | |
| 7,352,457 B2 | 4/2008 | Kvamme et al. | |
| 7,432,517 B2 | 10/2008 | Botma et al. | |
| 7,446,474 B2 | 11/2008 | Maldonado | |
| 7,465,935 B2 | 12/2008 | Urano et al. | |
| 7,525,649 B1 | 4/2009 | Leong et al. | |
| 7,528,943 B2 | 5/2009 | Brown et al. | |
| 7,609,309 B2 | 10/2009 | Brown et al. | |
| 7,741,666 B2 | 6/2010 | Nozaki et al. | |
| 7,750,280 B2 | 7/2010 | Hwang et al. | |
| 7,791,170 B2 | 9/2010 | Chiang et al. | |
| 7,813,406 B1 | 10/2010 | Nguyen et al. | |
| 7,875,948 B2 | 1/2011 | Hynecek et al. | |
| 7,928,382 B2 | 4/2011 | Hatakeyama et al. | |
| 7,952,633 B2 | 5/2011 | Brown et al. | |
| 7,985,658 B2 | 7/2011 | Lei et al. | |
| 7,999,342 B2 | 8/2011 | Hsu et al. | |
| 8,309,443 B2 | 11/2012 | Tanaka et al. | |
| 8,450,820 B2 | 5/2013 | Nanver | |
| 8,455,971 B2 | 6/2013 | Chen et al. | |
| 8,513,587 B2 | 8/2013 | Wang et al. | |
| 8,514,587 B2 | 8/2013 | Zhang et al. | |
| 8,624,971 B2 | 1/2014 | Brown et al. | |
| 8,629,384 B1 | 1/2014 | Biellak et al. | |
| 8,686,331 B2 | 4/2014 | Armstrong | |
| 8,754,972 B2 | 6/2014 | Brown et al. | |
| 8,803,075 B2 | 8/2014 | Menge et al. | |
| 8,891,079 B2 | 11/2014 | Zhao et al. | |
| 9,055,246 B2 | 6/2015 | Tay | |
| 2001/0017344 A1 | 8/2001 | Aebi | |
| 2002/0191834 A1 | 12/2002 | Fishbaine | |
| 2003/0222579 A1 * | 12/2003 | Habib et al. | 313/523 |
| 2004/0021061 A1 * | 2/2004 | Bijkerk | 250/214 R |
| 2004/0056279 A1 | 3/2004 | Niigaki | |
| 2004/0227070 A1 * | 11/2004 | Bateman et al. | 250/287 |
| 2005/0122021 A1 | 6/2005 | Smith et al. | |
| 2005/0167575 A1 | 8/2005 | Benz et al. | |
| 2005/0196059 A1 | 9/2005 | Inoue et al. | |
| 2005/0264148 A1 | 12/2005 | Maldonado et al. | |
| 2006/0055321 A1 | 3/2006 | Maldonado et al. | |
| 2006/0069460 A1 | 3/2006 | Smith et al. | |
| 2006/0170324 A1 | 8/2006 | Machuca | |
| 2006/0188869 A1 | 8/2006 | Zeskind et al. | |
| 2007/0002465 A1 | 1/2007 | Chuang et al. | |
| 2007/0034987 A1 | 2/2007 | Costello et al. | |
| 2007/0064135 A1 | 3/2007 | Brown et al. | |
| 2007/0096648 A1 | 5/2007 | Nakajima et al. | |
| 2007/0103769 A1 | 5/2007 | Kuwabara | |
| 2007/0188744 A1 | 8/2007 | Leslie et al. | |
| 2007/0291810 A1 | 12/2007 | Luo et al. | |
| 2008/0044932 A1 | 2/2008 | Samoilov et al. | |
| 2008/0173903 A1 | 7/2008 | Imai et al. | |
| 2008/0182092 A1 | 7/2008 | Bondokov et al. | |
| 2008/0267241 A1 | 10/2008 | Brown et al. | |
| 2008/0315092 A1 | 12/2008 | Kley | |
| 2008/0315121 A1 | 12/2008 | Nihtianov et al. | |
| 2009/0021717 A1 | 1/2009 | Nihtianov et al. | |
| 2009/0045325 A1 | 2/2009 | Tomuta et al. | |
| 2009/0091752 A1 | 4/2009 | Terasawa et al. | |
| 2009/0108207 A1 | 4/2009 | Liu | |
| 2009/0125242 A1 | 5/2009 | Choi | |
| 2009/0127995 A1 * | 5/2009 | Rosine | H01J 43/246 313/103 CM |
| 2009/0128912 A1 | 5/2009 | Okada | |
| 2009/0168152 A1 | 7/2009 | Gelernt et al. | |
| 2009/0180176 A1 | 7/2009 | Armstrong et al. | |
| 2010/0102213 A1 | 4/2010 | Garris | |
| 2010/0103409 A1 | 4/2010 | Ohshima et al. | |
| 2010/0148667 A1 | 6/2010 | Niigaki et al. | |
| 2010/0194956 A1 | 8/2010 | Yuan et al. | |
| 2010/0233869 A1 | 9/2010 | Park et al. | |
| 2010/0301437 A1 | 12/2010 | Brown | |
| 2010/0302424 A1 | 12/2010 | Yamaguchi | |
| 2011/0073982 A1 | 3/2011 | Armstrong et al. | |
| 2011/0101219 A1 | 5/2011 | Uchiyama et al. | |
| 2011/0116077 A1 | 5/2011 | Chuang et al. | |
| 2011/0169116 A1 | 7/2011 | Nanver et al. | |
| 2011/0234790 A1 | 9/2011 | True | |
| 2011/0256655 A1 | 10/2011 | Nikzad et al. | |
| 2011/0261354 A1 | 10/2011 | Sinfield | |
| 2011/0291109 A1 | 12/2011 | Wraback | |
| 2012/0012811 A1 | 1/2012 | DeFlumere | |
| 2012/0012957 A1 | 1/2012 | Larsen | |

(56) References Cited

U.S. PATENT DOCUMENTS

| | | |
|---|---|---|
| 2012/0038809 A1 | 2/2012 | Lee et al. |
| 2012/0081684 A1 | 4/2012 | Den Oef et al. |
| 2012/0132823 A1 | 5/2012 | Menge |
| 2012/0160993 A1 | 6/2012 | Nevet |
| 2012/0170021 A1 | 7/2012 | Walsh |
| 2012/0228485 A1 | 9/2012 | Iwakiri et al. |
| 2013/0009069 A1 | 1/2013 | Okada |
| 2013/0015324 A1 | 1/2013 | Park et al. |
| 2013/0016346 A1 | 1/2013 | Romanovsky et al. |
| 2013/0017205 A1 | 1/2013 | Giaccia et al. |
| 2013/0020491 A1 | 1/2013 | Mazzillo |
| 2013/0082241 A1 | 4/2013 | Kub et al. |
| 2013/0126705 A1 | 5/2013 | Maleev |
| 2013/0148112 A1 | 6/2013 | Chuang et al. |
| 2013/0056843 A1 | 7/2013 | Lee |
| 2013/0169957 A1 | 7/2013 | Wolf et al. |
| 2013/0176552 A1 | 7/2013 | Brown et al. |
| 2013/0264481 A1 | 10/2013 | Chern et al. |
| 2013/0270663 A1 | 10/2013 | Lin et al. |
| 2013/0313440 A1 | 11/2013 | Chuang et al. |
| 2013/0320211 A1 | 12/2013 | Park et al. |
| 2013/0336574 A1 | 12/2013 | Nasser-Ghodsi et al. |
| 2014/0034816 A1 | 2/2014 | Chuang et al. |
| 2014/0111799 A1 | 4/2014 | Lei et al. |
| 2014/0158864 A1 | 6/2014 | Brown et al. |
| 2014/0203386 A1 | 7/2014 | Bui |
| 2014/0204963 A1 | 7/2014 | Chuang et al. |
| 2014/0246595 A1 | 9/2014 | Menge |
| 2014/0291493 A1 | 10/2014 | Chuang |
| 2014/0362203 A1 | 12/2014 | Delaney |
| 2015/0177159 A1 | 6/2015 | Brown et al. |
| 2015/0200216 A1 | 7/2015 | Muramatsu et al. |
| 2015/0275393 A1 | 10/2015 | Bondokov et al. |
| 2015/0294998 A1 | 10/2015 | Nihtianov |

FOREIGN PATENT DOCUMENTS

| | | |
|---|---|---|
| EP | 1939917 A2 | 7/2008 |
| EP | 2346094 A1 | 7/2011 |
| JP | H05511287 A | 1/1993 |
| JP | H08241977 A | 9/1996 |
| JP | H09199075 A | 7/1997 |
| JP | 10-171965 A | 6/1998 |
| JP | 2002033473 | 1/2002 |
| JP | 200343533 A | 2/2003 |
| JP | 2004031452 A | 1/2004 |
| JP | 2007040909 A | 2/2007 |
| JP | 2007249092 A | 9/2007 |
| JP | 200298932 A | 11/2007 |
| JP | 2009117454 A | 5/2009 |
| KR | 100688497 | 3/2007 |
| KR | 100826407 | 5/2008 |
| RU | 2297070 C2 | 4/2007 |
| WO | 1995032518 A1 | 11/1995 |
| WO | 1996017372 A1 | 6/1996 |
| WO | 2007035858 A2 | 3/2007 |
| WO | 2008121232 A1 | 10/2008 |
| WO | 2011091159 | 7/2011 |
| WO | 2014067754 | 5/2014 |

OTHER PUBLICATIONS

Kenneth W. Tobin Inspection in Semiconductor Manufacturing Webster's Encyclopedia of Electrical and Electronic Engineering, vol. 10, pp. 242-262, Wiley & Sons, NY, NY, 1999.

Sobieski, Stanley, "Intensified Charge Coupled Devices for Ultra Low Light Level Imaging", NASA, Goddard Space Flight Center, SPIE vol. 78 (1976) Low Light Level Devices, pp. 73-77.

Certified copy of priority document U.S. Appl. No. 61/720,700, filed Oct. 31, 2012 corresponding to PCT/EP2013/071080 filed Oct. 9, 2013, pp. 1-44.

Sarubbi, F. et al. "Chemical Vapor Deposition of α-Boron Layers on Silicon for Controlled Nanometer-Deep p+ n Junction Formation", J. Electron. Mat., vol. 39, No. 2, Feb. 2010, pp. 162-173.

Nikzad, Shouleh et al., Delta-doped CCDs: High QE with long-term stability at UV and visible wavelengths, SPIE vol. 2198 (1994), pp. 907-915.

Hecht, Eugene, Optics, 4th Edition, India: Pearson Education Pte, Ltd. reprint 2004, 4 pages.

Hecht, Eugene, Optics, 2nd Edition, Adelphi University, 1987, Addison-Wesley Publishing Co., Inc., 3 pages.

Fu et al. "Optimizing GaN photocathode structure for higher quantum efficiency", Optik, vol. 123, No. 9, May 2012, pp. 756-768.

Howorth, J. R. et al. "Transmission silicon photoemitters and electron multipliers," Journal of Physics D: Applied Physics, vol. 9, No. 5, Apr. 1, 1976, pp. 785-794.

Allen, F. G. et al. "Work Function, Photoelectric Threshold, and Surface States of Atomically Clean Silicon", Physical Review, vol. 127, No. 1, Jul. 1, 1962, pp. 150-158.

Henderson, Brian S. "Study of Negative Electron Affinity GaAs Photocathodes", Department of Physics and Astronomy, Rice University, Houston, TX, Aug. 7, 2009, 18 pages.

Martinelli, Ramon U. "Reflection and Transmission Secondary Emission from Silicon", Applied Physics Letters, vol. 17, No. 8, Oct. 15, 1970, pp. 313-314.

Martinelli, Ramon U. "Infrared Photoemission from Silicon", Applied Physics Letters, vol. 16, No. 7, Apr. 1, 1970, pp. 261-262.

Sarubbi F et al: "Pure boron-doped photodiodes: a solution for radiation detection in EUV lithography", Proceedings of the 38th European Solid-State Device Research Conference: Edinburgh International Conference Centre, Endiburgh, Scotland, UK, Sep. 15-19, 2008, Piscataway, NJ: IEE, US, Sep. 15, 2008, pp. 278-281.

KLA-Tencor Corporation; PCT International Search Report dated Dec. 8, 2015 for Application No. PCT/US2015/047307, 3 pages.

KLA-Tencor Corporation; PCT International Search Report dated Dec. 29, 2015 for Application No. PCT/US2015/051538, 3 pages.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Fu, Xiaoqian, "Higher Quantum Efficiency by Optimizing GaN Photocathode Structure", 978-1-4244-6644-3/10/ © 2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Utsumi, Vacuum Microelectrnoics: What's New and Exciting, IEEE vol. 38, No. 10, Oct. 1991, 8 pgs.

Armstrong, Carter M., The Quest for the Ultimate Vacuum Tube, Spectrum IEEE, Dec. 2015, 4 pgs.

Serbun, Pavel et al., Stable field emission of single B-doped . . . , JVSTB, 31, 02B101 (2013); doi: 10.1116/1.4765088, 7 pgs.

(56) References Cited

OTHER PUBLICATIONS

Sato, T. et al., Fabrication and characterization of HfC coated . . . , J. Vac. Sci. Technol. B 2194), published Jul. 31, 2003, 5 pgs.
Nagao, Masayoshi, Fabrication of a Field Emitter Array with a Built-In Einzel Lens, JJAP 48 (2008) 06FK02, 4 pgs.
Rakhshandehroo, M.R., et al., Fabrication of a self-aligned silicon field emission . . . , JVSTB, 16, 765 (1998); doi: 10.1116/1,589900, 6 pgs.
Rakhshandehroo, M.R., et al., Field emission from gated Si emitter tips with precise . . . , JVSTB, 15, 2777 (1997); doi: 10.1116/1.589726, 6 pgs.
Ding, Meng, Field Emission from Silicon, MIT 2001, 277 pgs.
Koike, Akifuni, Field Emitter Equipped With a Suppressor to Control Emission Angel, IEEE Electron Device Letters, vol. 34, No. 5, May 2013, 3 pgs.
Nagao, Masayoshi, Cathode Technologies for Field Emission Displays, IEJ Trans 2006; 1:171-178, 8 pgs.
Neo, Yoichiro, Electron Optical Properties of Microcolumn with Field Emitter, JJAP 52 (2013) 036603, 5 pgs.
Fowler, R.H. et al., Electron Emission in Intense Electric Fields, Mar. 31, 1928, 9 pgs.
Fanton, J. T., et al., "Multiparameter Measurements of Thin Films Using beam-profile reflectometry", Journal of Applied Physics, vol. 73, No. 11, p. 7035 (1993).
Pain et al., "A Back-Illuminated Megapixel CMOS Image Sensor", Jun. 9, 2005, IEEE Workshop on Charge-Coupled Devices and Advanced Image Sensors, Karuizawa, Japan, 4 pgs.

\* cited by examiner

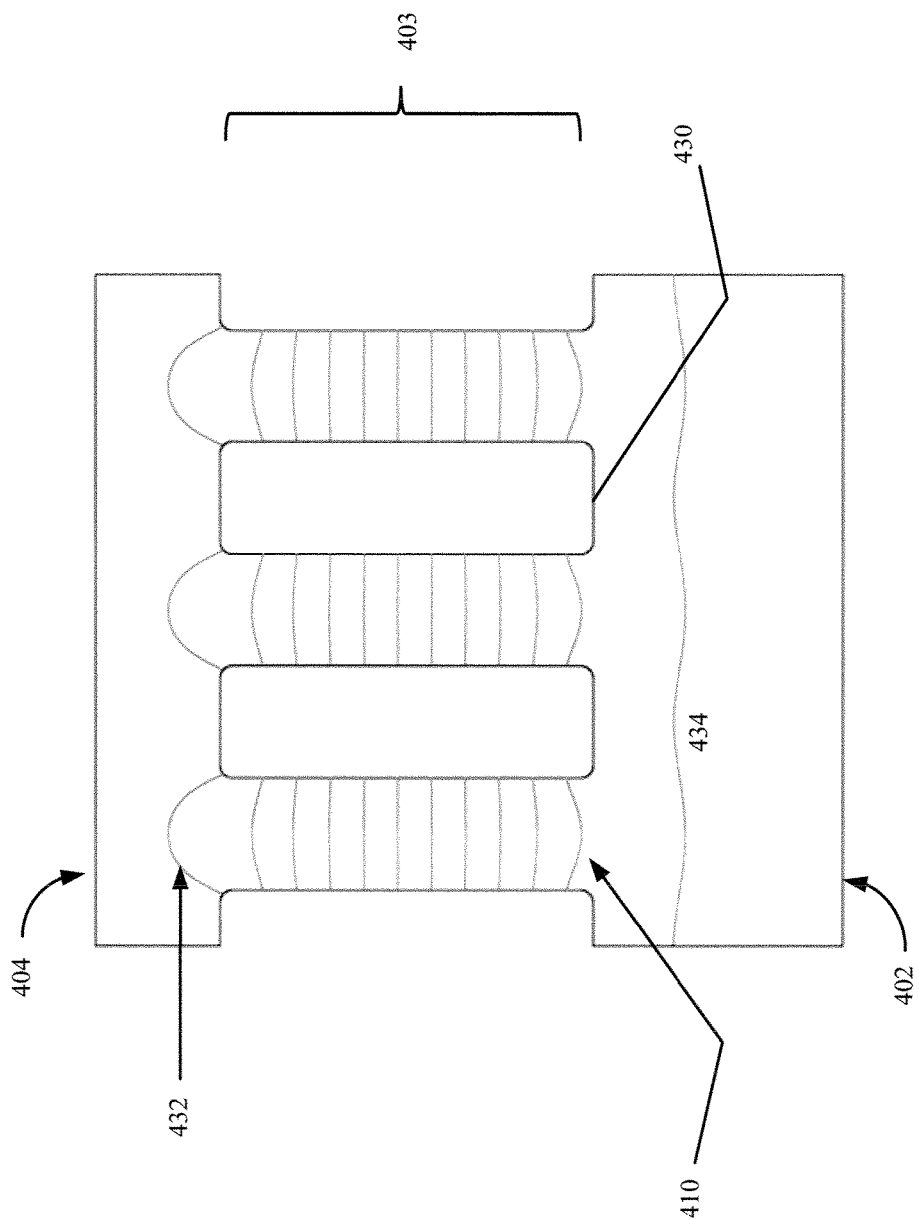

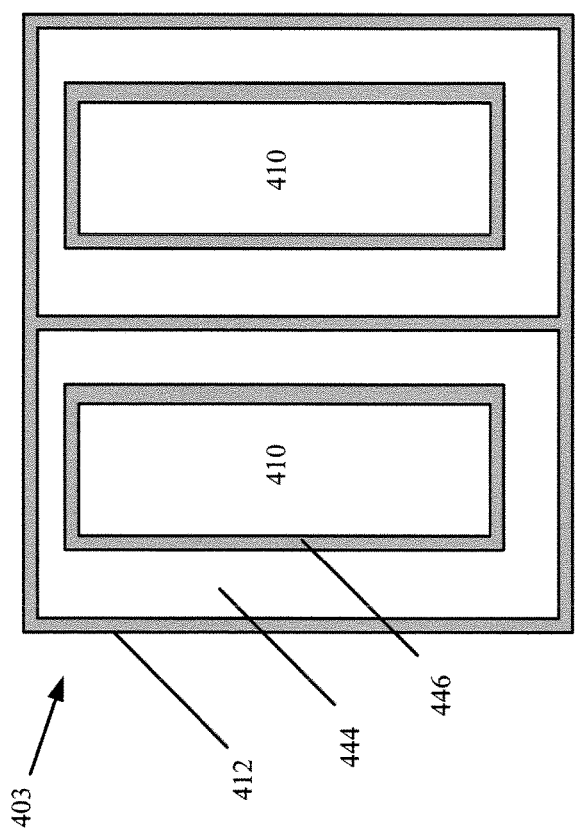
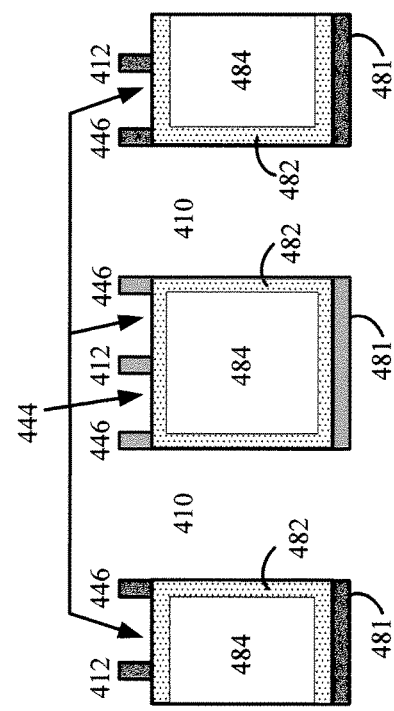

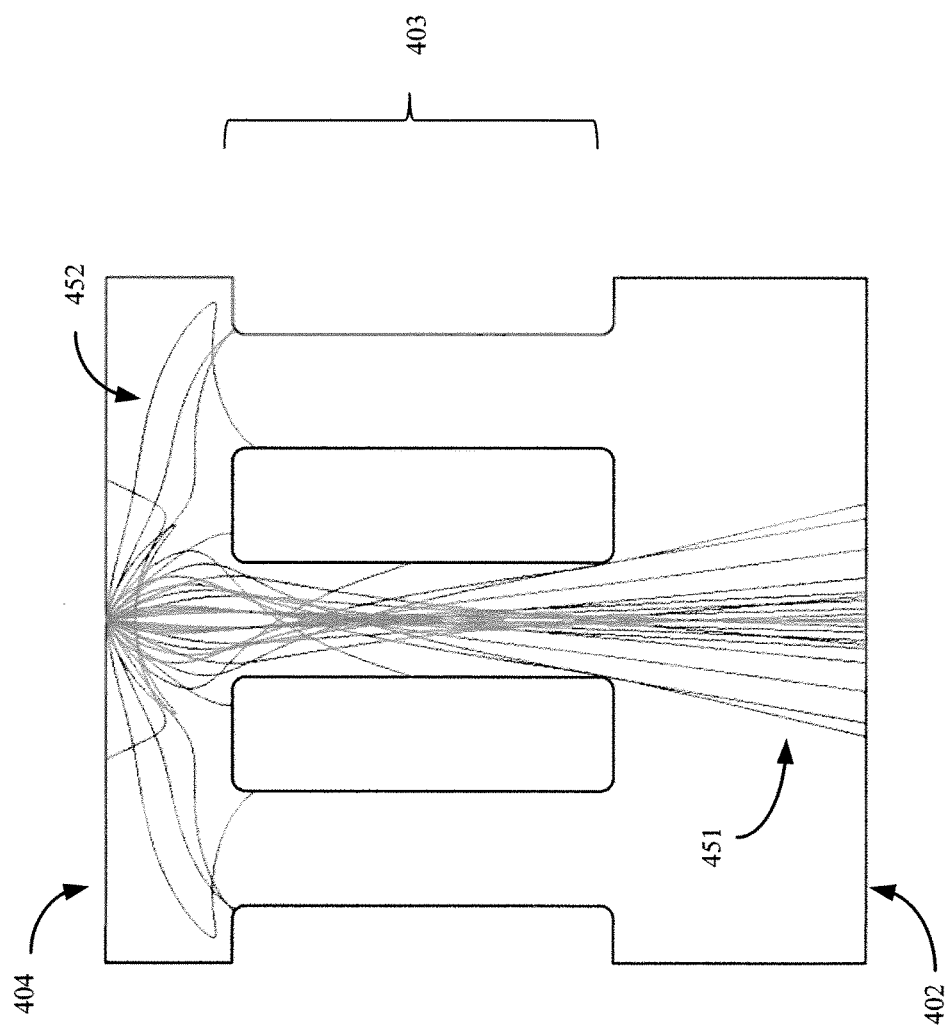

ELECTRON-BOMBARDED CHARGE-COUPLED DEVICE AND INSPECTION SYSTEMS USING EBCCD DETECTORS

RELATED APPLICATION

The present application claims priority to U.S. Provisional Application 61/569,611, entitled "Electron-Bombarded CCD And Inspection Systems Using Electron-Bombarded CCD Detectors" and filed Dec. 12, 2011, which is incorporated by reference herein.

BACKGROUND OF THE DISCLOSURE

The disclosure relates to a light-sensitive array detector capable of detecting extremely low levels of light with high spatial resolution, high quantum efficiency, very good signal to noise ratio, and high dynamic range.

RELATED ART

Electron-bombarded charge-coupled device (EBCCD) detectors are known in the art. FIG. 1A illustrates a conventional EBCCD 101 including a sealed tube 105 that encloses a light-sensitive photocathode 104 and a CCD 102 in a vacuum environment. Typically, the gap between photocathode 104 and CCD 102 is about 1 or 2 mm. Sealed tube 105 has a window positioned adjacent to photocathode 104 such that in the presence of incident light 110, photocathode 104 can absorb a photon from incident light 110 and then emit one or a few electrons 112.

In a typical configuration, photocathode 104 is held at a negative potential of about −2000 V to −10,000 V relative to CCD 102. Because of the potential difference, electrons 112 are accelerated towards CCD 102. When an electron strikes CCD 102, the electron typically generates multiple electron-hole pairs in the semiconductor material of CCD 102. The electrons are captured by CCD 102 and subsequently converted to a current or voltage when CCD 102 is read out by the detector.

Image intensified detectors are also known in the art. An image intensifier is similar to an EBCCD, except instead of a CCD, there is a phosphor screen and an output window. An external image detector, such as a CCD or a CMOS imaging device can capture the light from the phosphor screen.

Photomultiplier tubes are also known in the art. A photomultiplier can have very high gain and, in some cases, can detect a single captured photon. However, an individual photomultiplier tube has no spatial resolution. Although photomultiplier arrays can be fabricated, they are large, expensive, and have spatial resolutions in millimeters rather than microns.

Micro-channel plate (MCP) detectors are also known in the art. MCPs may used individually, or may be cascaded to increase the gain. FIG. 1B illustrates a cross-sectional view of a conventional MCP assembly 121 including two cascaded MCPs 140 and 142. A typical MCP is fabricated from a highly resistive material and may be 1 to 2 mm thick. An MCP contains an array of small holes having diameters of approximately 4 to 10 μm, with the holes separated by approximately 6 to 20 μm. The holes are intentionally typically tilted at a few degrees relative to a perpendicular to the surface of the MCP to ensure maximum secondary electron emission (described in greater detail below). As shown in FIG. 1B, the holes of MCP 140 and 142 are tilted in opposite directions to block, or at least minimize, the straight-line paths for ions through the cascaded MCP stack. A bottom surface 146 of MCP 140 can be held at a positive potential relative to its top surface 145, e.g. a few hundred volts to 1 or 2 kV. MCP 142 can be held at a more positive potential than MCP 140. In general, when cascaded MCPs are used, each successive MCP is held at a more positive potential than the previous, going from the input to output.

In operation, when an electron 131 strikes the wall of one of the holes, secondary electrons are emitted in many different directions. Those secondary electrons are accelerated towards the lower surface because of the potential difference from top to bottom of the MCP. Some of those secondary electrons strike the wall of the hole and create more secondary electrons. This process can happen multiple times in a single MCP. Indeed, a single incoming electron or photon may create many hundreds or even a thousand secondary electrons moving in different directions. In the case of cascaded MCPs 140 and 142, secondary electrons 132, numbering from 100,000 to 1,000,000, may be generated from a single incident electron or photon. MCPs may be used in an image intensifier or EBCCD with a photocathode, or if the incoming photon energy is sufficient, without a photocathode.

Unfortunately, the above-described detectors have poor spatial resolution, which significantly limits their use in semiconductor inspection applications. For example, in conventional EBCCD detectors, the electrons will spread in a horizontal direction as they accelerate towards the CCD. In applications sensing UV light, which is used in semiconductor inspection, the incoming photons have energies of about 3.5 eV or greater. Because the work function of the photocathode may be only 1 or 2 eV, electrons will be generated with energies of 1 or several eV. Notably, even an energy as low as 1 eV corresponds to an electron velocity of about $6 \times 10^5$ ms$^{-1}$.

Electrons are emitted essentially randomly in direction, so most electrons are emitted with a significant horizontal velocity component. Under an accelerating field gradient of $10^6$ V m$^{-1}$ (1 kV across a 1 mm gap), an electron will take about 100 ps to cross the above-described 1 mm gap from the photocathode to CCD. In that 100 ps, the sideways motion of a typical electron will be about 50 μm due to its horizontal component of velocity. Because there will be a distribution of horizontal velocities from zero to a maximum that depends on the initial electron energy, a blurring of the image on scale lengths of about 50 μm to 100 μm may occur. This blurring will increase for shorter wavelengths of incident light as the initial photon energy will be greater.

Thus, as the semiconductor industry moves to shorter wavelengths for inspection, this blurring will get worse. Even with 355 nm incident radiation, a spatial resolution of 20 μm cannot be achieved at the detector. With 266 nm incident radiation, the blurring will be significantly worse. Narrowing the gap between the photocathode and CCD increases the risk of arcing or electrical breakdown, thereby decreasing the reliability of the device. Increasing the voltage difference also degrades reliability as well as accelerating the wear-out mechanism described below.

Reducing the gap between the photocathode and the CCD will reduce the image blur. However, thinned CCDs have many tens of microns of warp due to stresses. Unless the gap is much larger than the warp of the CCD, the image will be distorted in different locations by the electric field variations that result from different gaps in different locations.

Another limitation of existing EBCCD detectors is the generation of an ion whenever an electron collides with an atom of residual gas in the vacuum, or when an electron dislodges an atom from the surface or bulk of the CCD. These ions are accelerated back towards the photocathode by the potential difference and strike the photocathode, thereby ablating material and causing additional electrons to be ejected. This ablation of the photocathode reduces the lifetime and the efficiency of the photocathode.

Specifically, as the photocathode gets thinner, the probability of a photon passing through without absorption increases. However, the photocathode is already manufactured to be thin so that the electrons have a very high probability to escape from the material without being absorbed, otherwise the quantum efficiency will be low. Therefore, the ablation of the photocathode can lead to material failure. Furthermore, the extra electrons generated during the ablation, although increasing the signal level, degrade the signal to noise ratio (i.e., ion creation is a random event creating significant numbers of electrons, thereby leading to non-Gaussian noise statistics).

The lifetime of a conventional EBCCD can also be limited by the damage done to the CCD by the high energy electrons striking it.

Non-flatness of the CCD can cause different electric field gradients in different regions of the CCD. These electric field gradient differentials can result in small distortions of the image as transferred from the photocathode to the CCD and/or local variations in gain of the EBCCD detector.

Because of the high voltage difference between the photocathode and the CCD, any spikes on the photocathode surface will experience very high electric field gradients and may spontaneously generate electrons by field emission. This electron generation will appear on the EBCCD as a "hot spot" with signal output even in the complete absence of light.

An image intensifier will typically have worse image resolution than an EBCCD because the transfer of the light from the phosphor to the image detector will add an additional blur. This additional blurring usually offsets any small improvement in lateral resolution due to the use of higher accelerating voltages. An image intensifier can protect the image detector from high energy electrons and from high-voltage arcing, but ablation of the photocathode and excess noise generation still occur due to sputtering of the phosphor.

Photomultiplier arrays are severely limited in lateral resolution (mm scale resolution) and are prohibitively expensive to fabricate in arrays containing many hundreds or thousands of detectors.

MCPs have poor lateral resolution due to the generated secondary electrons. As noted above, the secondary electrons are created with energies of many eV, and therefore have horizontal velocity components that can be many times greater than $6\times10^5$ m s$^{-1}$. Indeed, the horizontal spreading of the secondary electrons as they traverse towards the CCD or phosphor can be 100 µm or more even with a single MCP (and will be much greater for cascaded MCPs). Therefore, the horizontal spreading of the secondary electrons is much worse than for an EBCCD or an image intensifier without a MCP. Moreover, although MCPS are capable of very high gain, that gain is very noisy. Each incoming photon or electron can generate very different numbers of secondary electrons.

Therefore, an EBCCD is needed that has improved spatial resolution, improved lifetime, and improved signal to noise, while maintaining, or improving, the quantum efficiency.

SUMMARY

An electron-bombarded charge-coupled device (EBCCD) includes an assembly with a window, a photocathode inside the assembly and adjacent to the window, and a CCD device inside the assembly and positioned to collect electrons emitted from the photocathode. The EBCCD further includes a control device positioned between the photocathode and the CCD. The control device has a plurality of holes therein, wherein the plurality of holes are formed perpendicular to a surface of the photocathode, and wherein a pattern of the plurality of holes is aligned with a pattern of pixels in the CCD. Each hole is surrounded by at least one first electrode, which is formed on a surface of the control device facing the photocathode.

The photocathode may be a coating on the window. The CCD may include a back-thinned CCD or a time-delay integration CCD. The exterior surface of the window may include an antireflective coating. The control device may include a silicon structure or a metallic structure.

In one embodiment, the control device may include a plurality of ridges between the holes. The control device may be separated from the photocathode by approximately half a shorter dimension of a CCD pixel or less. In one embodiment, a plurality of first electrodes may be provided, wherein each first electrode surrounds a given hole and is separated from the given hole by a gap. In another embodiment, a plurality of ring electrodes and one surface electrode are provided, wherein each of the ring electrodes is separated from a given hole by a first gap, and is separated from the surface electrode by a second gap. In yet another embodiment, at least one second electrode surrounds the holes of the control device and is positioned on a surface of the control device facing the CCD.

A method of operating the EBCCD is also provided. This method includes holding a photocathode of the EBCCD at a negative voltage relative to a CCD of the EBCCD. The electrons are focused as they travel from the photocathode towards pixels of the CCD. Moreover, the holes of a control device, which provide the focusing, are aligned with the pixels of the CCD.

The method further includes holding the inside surfaces of the holes of the control device at a positive voltage relative to the photocathode. In one embodiment, a first electrode surrounding at least one hole is held at a different voltage than the inside surfaces of the holes. This first electrode is positioned on a surface of the control device facing the photocathode. Specifically, the first electrode is held at a negative voltage relative to the inside surfaces of the holes. In another embodiment, a second electrode is held at a different potential from the first electrode. The second electrode surrounds at least one hole of the control device and is positioned to face the CCD. In yet another embodiment, some regions of a surface of the control device closest to the photocathode are held at a potential similar to that of the photocathode or slightly negative relative to the photocathode.

A dark-field inspection system including the focusing EBCCD with control device is provided. This system includes optics for directing light to a sample being inspected, optics for collecting scattered light from the sample and directing collected light, and the described focusing EBCCD for receiving the collected light. In one embodiment, the CCD is a time-delay integration CCD. The time-delay integration CCD may include multiple readout registers that are readable in parallel.

A method of inspecting a semiconductor wafer is also provided. This method includes illuminating a region of the wafer with light, collecting the scattered light from the wafer, and directing the collected light to a focusing EBCCD detector. In one embodiment, the CCD performs time-delay integration. The time-delay integration may read out multiple registers in parallel.

BRIEF DESCRIPTION OF THE DRAWINGS

FIG. 4C illustrates a cross-sectional view of three holes of one EBCCD and their exemplary equipotentials.

FIGS. 4D(1) AND 4D(2) illustrate a top view and a cross section, respectively, of another exemplary control device.

FIG. 4E illustrates calculated electron trajectories for the exemplary EBCCD of FIGS. 4C and 4D for electrons leaving the photocathode in different directions.

DETAILED DESCRIPTION OF THE DRAWINGS

Figure 1A:
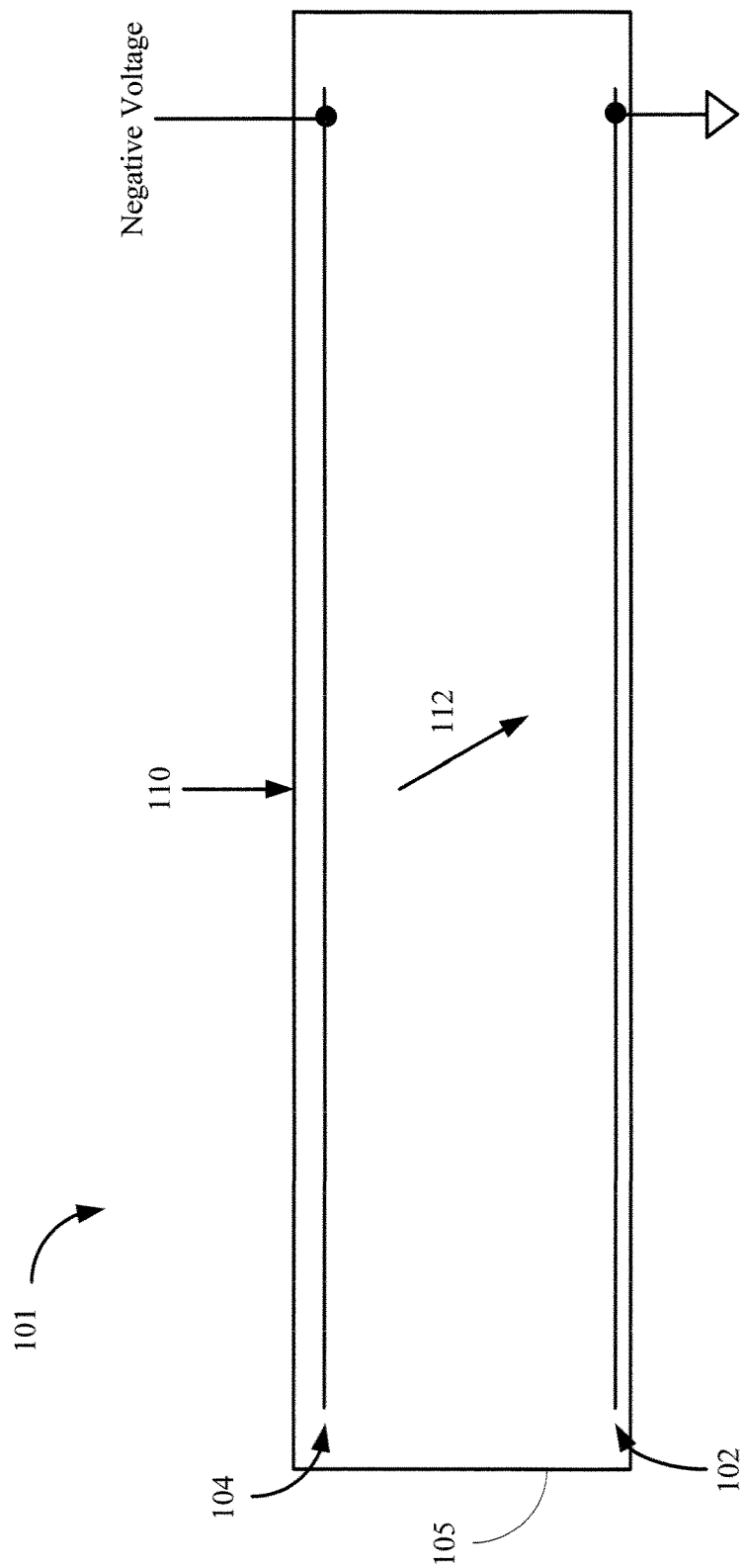
FIG. 1A illustrates a conventional EBCCD.
Figure 1B:
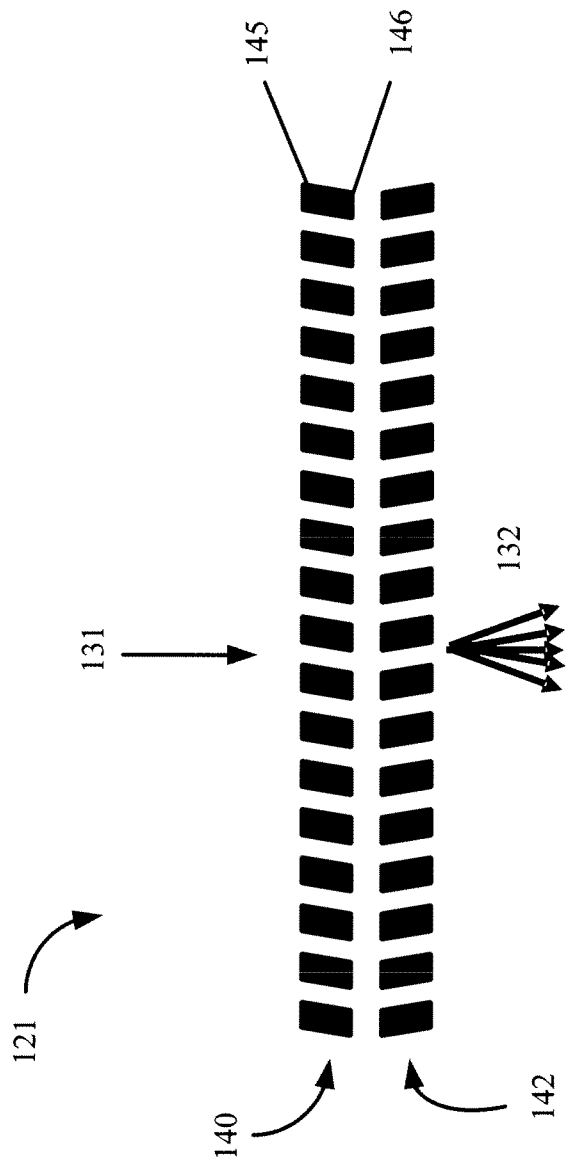
FIG. 1B illustrates a cross-sectional view of a conventional MCP assembly including two cascaded MCPs.
Figure 2:
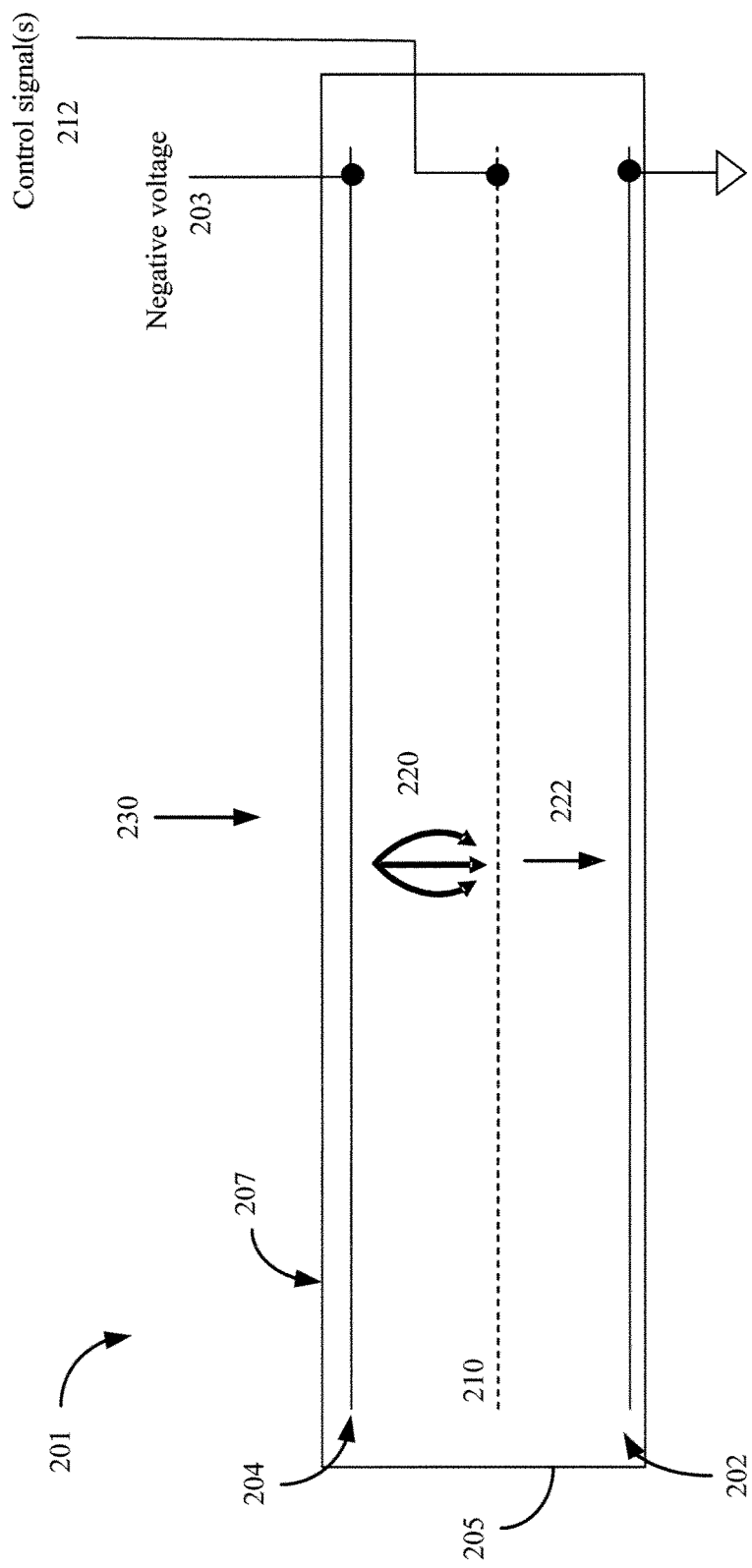
FIG. 2 illustrates an exemplary focusing EBCCD including a control device.

A focusing EBCCD has improved spatial resolution, improved lifetime, and improved signal to noise, while maintaining, or improving, the quantum efficiency. FIG. 2 illustrates a focusing EBCCD 201 including a sealed tube 205 that encloses a light-sensitive photocathode 204 and a CCD 202 in a vacuum environment. A top surface of tube 205 comprises a window 207 that is transparent at the wavelengths of interest. For UV sensitive EBCCD detectors, this window preferably comprises a very pure grade of quartz, fused silica, or alumina (sapphire). In some preferred embodiments, the outside surface of the window is coated with a UV anti-reflection coating. Such a coating may be a single layer of a low index material, such as magnesium fluoride ($MgF_2$), or a multi-layer coating.

Photocathode 204 is positioned immediately adjacent to window 207 or may be implemented as a coating of window 207. The photocathode material may be substantially similar to any photocathode material known in the art for use in photomultiplier, image intensifier, or CCD detectors. In preferred embodiments, photocathode 204 may comprise one or more alkali metals such as Cesium, or may comprise a semiconductor such gallium nitride (GaN) or gallium arsenide (GaAs). Photocathode 204 is held at a negative voltage 203 relative to CCD 202. In some embodiments, negative voltage 203 may be approximately 1000 V. In other embodiments, negative voltage 203 may be a few hundred volts or several tens of volts.

CCD 202, which is positioned near a bottom surface of tube 205, is a thinned CCD oriented so that the electrons impinge first on its back surface (i.e. a back-thinned CCD). A back-thinned CCD is typically formed by forming transistors and other devices on top of a silicon substrate of, for example, approximately 500 μm thick. Doping can be used for creating both p-type and n-type devices. Because these devices are formed from a variety of materials of different thicknesses, some of the electrons reaching the CCD may be blocked or absorbed by these devices as well as by the thick silicon. Therefore, a significant portion of the silicon is removed to ensure that as many of the electrons as possible can be detected when the electrons impinge on the back surface. In standard embodiments, the thickness of the resulting silicon is on the order of 25 μm.

Unfortunately, native oxide will form on any exposed silicon. This native oxide may also inhibit the electrons from entering the silicon. Therefore, in one embodiment, to facilitate enhanced detection using the CCD, a Boron coating can be provided on any exposed silicon that would otherwise form native oxide thereon. This protective coating is described in detail in U.S. Provisional Application 61/658,758, which was filed on Jun. 12, 2012 and is incorporated by reference herein. In some embodiments, CCD 202 is a time-delay integration (TDI) CCD. In some preferred embodiments, CCD 202 is held close to ground potential.

To provide the focusing, and thus improved performance, EBCCD 201 further comprises a control device 210, which is controlled by one or more control signals 212 (e.g. control voltages). In one embodiment, control device 210 is positioned between photocathode 204 and CCD 202. In another embodiment, control device 210 is attached to CCD 202.

Control device 210 can advantageously focus electrons traveling from photocathode 204 towards CCD 202 to minimize the horizontal spread of the electrons. In some embodiments, control device 210 may block rather than focus some electrons with large horizontal velocity components. To provide this focusing, control device 210 has an array of through holes (i.e. apertures). In one embodiment, the pattern of the holes is aligned with the pattern of the pixels in CCD 202. For example, if CCD 202 comprises square pixels of 20 μm by 20 μm, then control device 210 may comprise an array of approximately 10 μm diameter holes on a 20 μm by 20 μm grid. Control device 210 may be approximately 25 μm to 200 μm thick in some embodiments. Control device 210 may further comprise alignment features to allow alignment of the array of holes to the array of pixels in CCD 202. Similarly, CCD 202 may incorporate alignment marks on one or both of its surfaces to facilitate alignment with control device 210.

In some embodiments, control device 210 may comprise a metal plate or foil. In other preferred embodiments, control device 210 may comprise a silicon crystal or wafer. The holes may be fabricated in control device 210 by laser drilling (for example, for metallic material(s)) or by photolithography and etching (for example, for semiconductor material(s)). In embodiments where control device 210 is fabricated using semiconductor technology, elements other than the holes can also be formed thereon as well as therein. For example, electrodes, doping areas, voltage control devices, and detection devices may be formed on or in control device 210.

As described above, a microchannel plate (MCP) generates secondary electrons, which increase the gain of the device but degrade its spatial resolution. In contrast, control device 210 focuses the majority of the electrons towards pixels of CCD 202, while blocking or deflecting electrons that have a significant horizontal velocity component. In some preferred embodiments, the potential difference between photocathode 204 and a top surface of control device 210 is small, such as a few volts or a few tens of volts, so that any electrons that do strike a control electrode of control device 210 generate no, or only a few, secondary electrons.

When light 230 is incident on EBCCD 201, one or more electrons 220 are emitted from photocathode 204. These electrons, which are emitted in substantially all directions, are accelerated towards control device 210 by the potential difference between photocathode 204 and control device 210. The holes in control device 210 substantially collimate the electrons in control device 210. Therefore, when the electrons emerge from control device 210, the electrons are traveling substantially perpendicularly to CCD 202, thereby ensuring that most electrons that travel through a given hole land on the corresponding (and aligned) pixel of CCD 202, thereby substantially reducing the image blur.

Figure 3A:
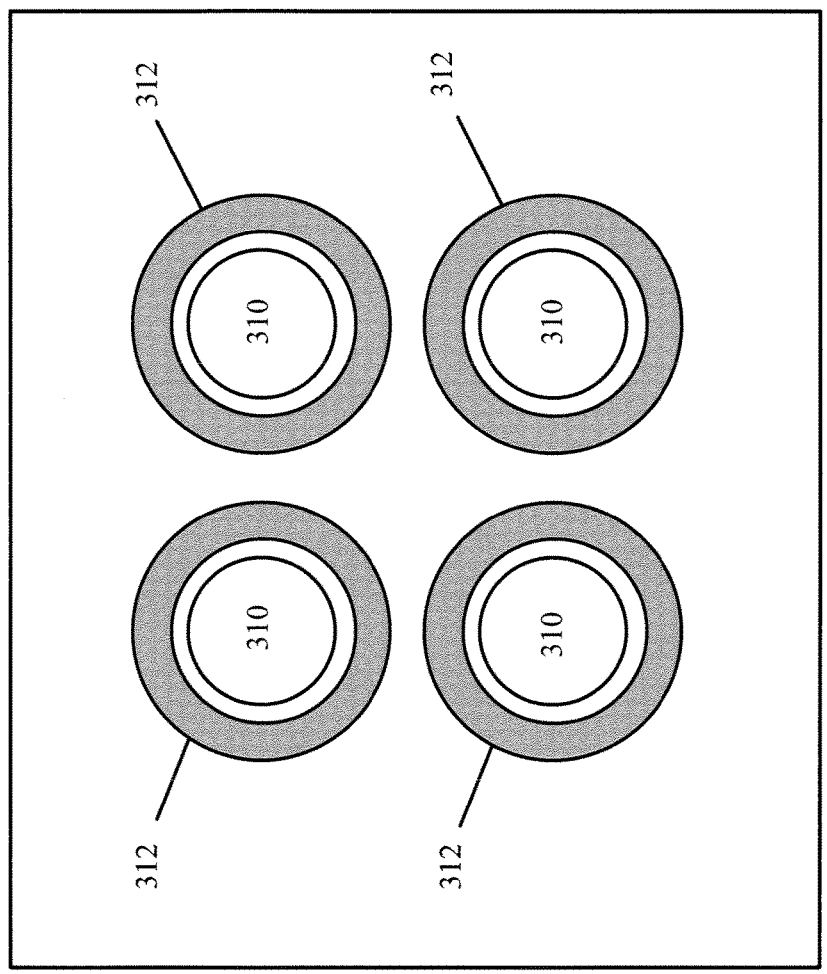
FIG. 3A illustrates a top view of four holes in an exemplary control device.

FIG. 3A illustrates a top view of four holes 310 in an exemplary control device. As described above, these holes are preferably laid out on a grid that matches the grid of pixels in the CCD. Note that if the detector is a line detector, rather than an area detector, then there may be only a single line of holes. In preferred embodiments, these holes have a diameter that is approximately one half of the size of the CCD pixel. By way of example, but not as a limitation, if the CCD has pixels that are 20 µm by 20 µm, then the diameter of each hole might be about 10 µm in some embodiments. In some embodiments, the control device is between about 2.5 and 20 times thicker than the diameter of hole. For example if the COD pixel size is approximately 20 µm by 20 µm, then the hole diameter might be approximately 10 µm, and the thickness of the control device might be between about 25 µm and about 200 µm. Because the hole length is much greater than the hole diameter, electrons that travel through the hole must be traveling in a relatively narrow range of angles.

Surrounding each hole 310 is an electrode 312. In preferred embodiments, the inside surface of hole 310 is conducting and is connected to a control voltage. In some embodiments, this voltage is positive relative to the photocathode so as to attract electrons towards hole 310 (as shown figuratively in FIG. 2 by the arrows representing electrons 220). The electrode 312 is at a different voltage from the inside surface of hole 310 so as to direct electrons towards hole 310. In some embodiments, electrode 312 is at a negative voltage relative to the inside surface of hole 310. In some embodiments, two or more electrodes are provided around each hole 310. In some embodiments, an electrode is also provided around each hole on the bottom surface of the control device.

Figure 3B:
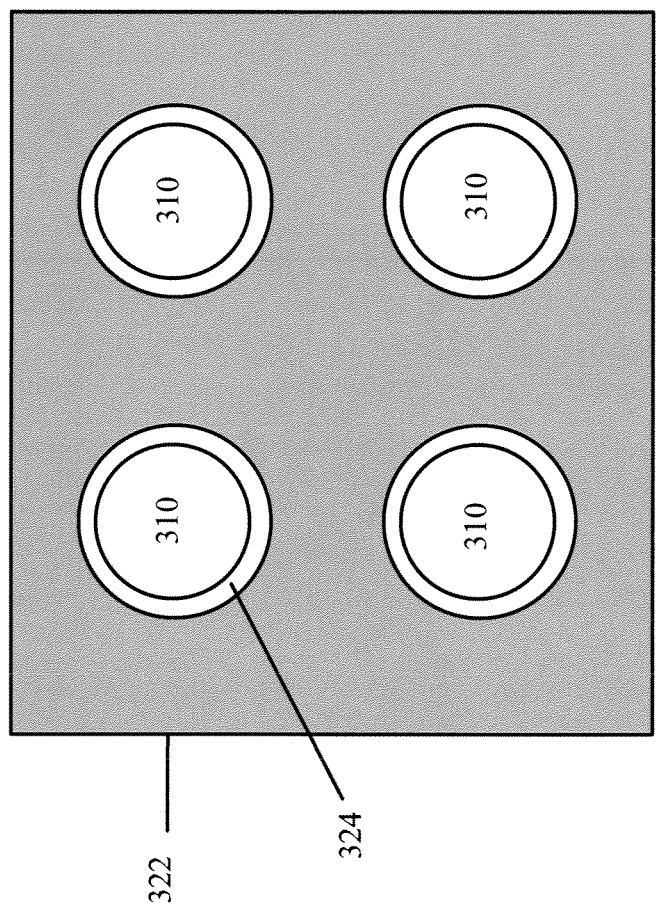
FIG. 3B illustrates a top view of another control device in which individual electrodes have been merged to form a single surface electrode that covers much of the upper surface of the control device.

FIG. 3B illustrates an alternative embodiment of the control device in which individual electrodes (e.g. electrodes 312 shown in FIG. 3A) have been merged to form a single electrode 322 that covers much of the upper surface of the control device. In some embodiments, there may be a small gap 324 between surface electrode 322 and each hole 310. Gap 324 may be formed by a doped semiconductor (n-type or p-type doping with standard dopants), which provides a weak conductive element having a potential varying from outside to inside. Note that gap 324 is not formed as an insulator, which would tend to capture electrons and eventually become negatively charged, thereby repelling instead of attracting electrons to holes 310.

Figure 3C:
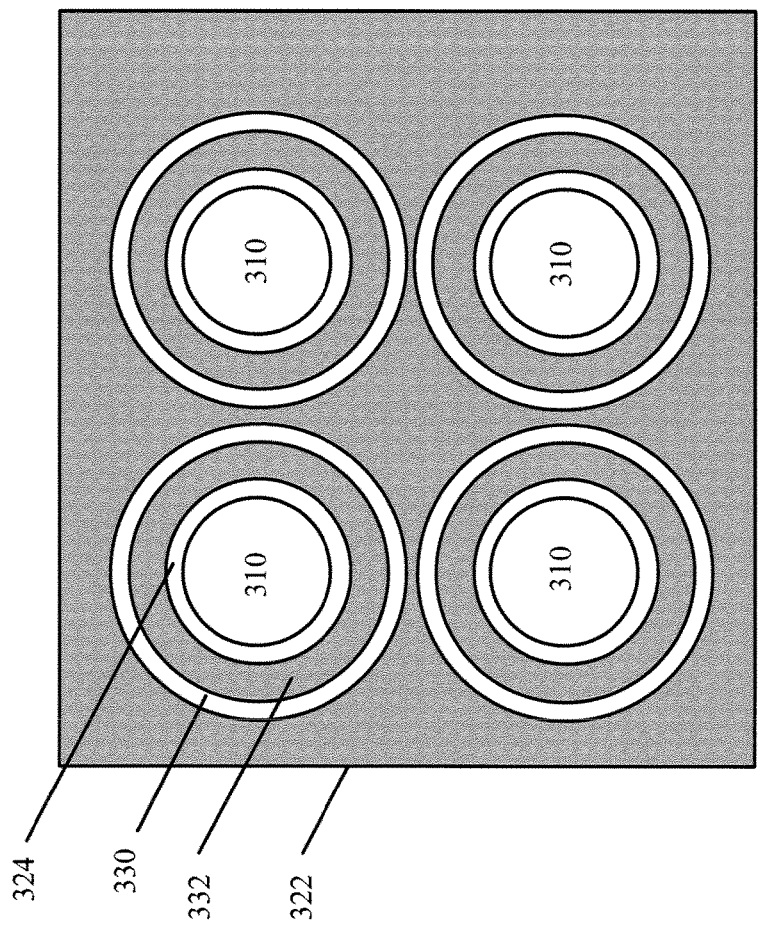
FIG. 3C illustrates a top view of yet another control device including an inner electrode provided between a surface electrode and each hole.

FIG. 3C shows yet another embodiment of the control device. In this embodiment, an inner electrode 332 is provided between a surface electrode 322 and each hole 310. Inner electrodes 332 and surface electrode 322 are separated by small gaps 330. In one embodiment, inner electrodes 332 and holes 310 may be separated by small gaps 324. In preferred embodiments, gaps 324 (as well as other gaps discussed herein) and other substantially non-conducting areas on the surfaces of the control device are lightly doped or coated with a weakly conductive material to avoid charge up of those surfaces from electrons or ions hitting those surfaces.

Figure 4A:
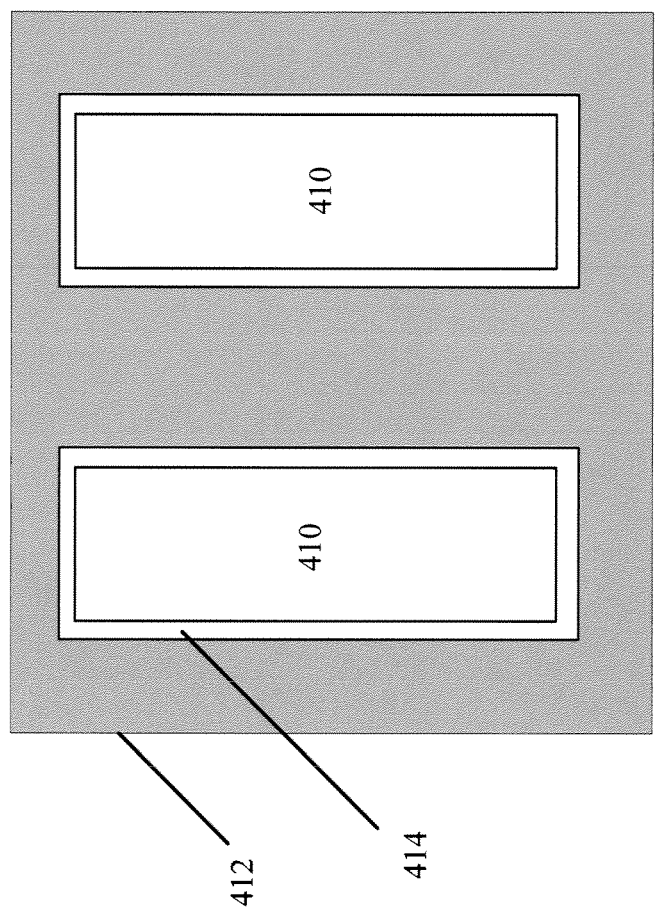
FIG. 4A illustrates a top view of an exemplary control device suitable for use in a line detector EBCCD.

FIG. 4A illustrates a top view of an exemplary control device suitable for use in a line detector EBCCD. Instead of the two-dimensional array of substantially circular holes used for an area detector, a one dimensional array of substantially rectangular holes 410 (or slits) may be used. Holes 410 are surrounded by a single surface electrode 412, or multiple electrodes (not shown). Small gaps 414 may be provided between each hole 410 and any electrode(s). As discussed above, the material comprising gap 414 may be lightly doped so as to be weakly conductive, thereby preventing charge up. In some embodiments of a line detector, the width of holes 410 is approximately half of the width of a pixel on the CCD, thereby minimizing the image blur in the direction along the linear array. In some embodiments, the length of holes 410 is approximately 75% to 90% of the length of the pixels on the CCD to maximize the transmission of electrons (because blur perpendicular to the linear array axis is less important).

Figure 4B:
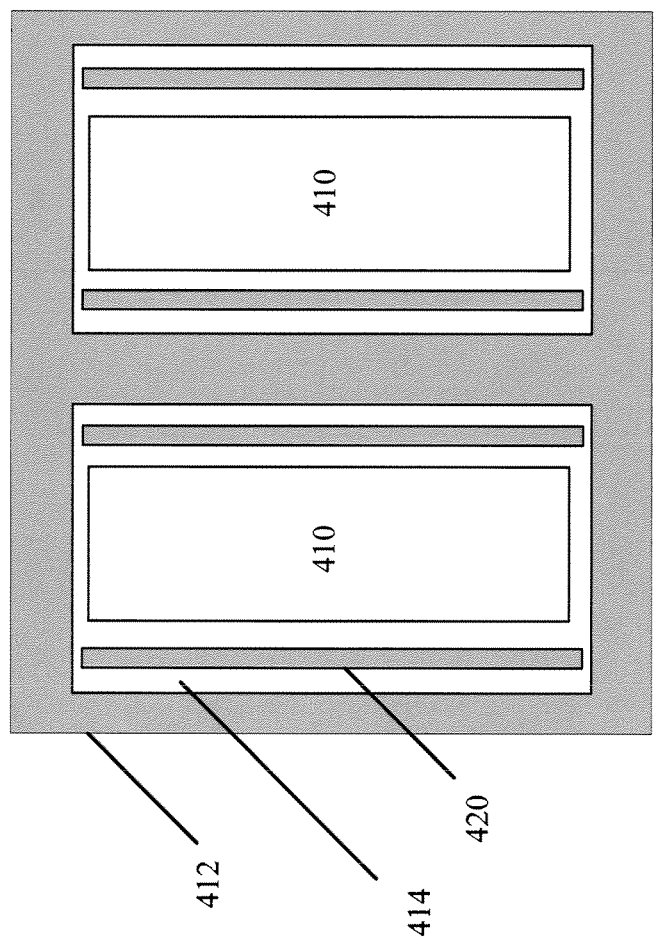
FIG. 4B illustrates a top view of another exemplary control device suitable for use in a line detector EBCCD.

FIG. 4B illustrates another exemplary control device suitable for use in a line detector EBCCD. In this embodiment, additional electrodes 420 are placed either side of each hole 410, or surrounding the hole (not shown).

It is to be understood that the above examples are merely by way of illustration and should not be interpreted as limiting the scope of the invention. It will be appreciated that many different electrode, gap, and hole configurations are possible. For example, in one embodiment, more than two electrodes surround or are adjacent to each hole. Thus, different configurations of electrodes, gaps, and holes are within the scope of this invention.

FIG. 4C illustrates a cross-sectional view of three holes of an exemplary embodiment of an EBCCD. In this embodiment, a photocathode 404 is held at a potential of approximately −60 V, and a CCD 402 is held at a potential of approximately 0 V. Also, assuming a linear detector embodiment, the pixel width of CCD 402 is approximately 18 µm, whereas the pixel length (perpendicular to the plane of FIG. 4C) is much greater than 18 µm, e.g. approximately 100 µm or larger. A control device 403 includes an array of holes 410 (e.g. slits), which are aligned with the pixels of CCD 402. Each hole 410 is approximately 9 µm wide (i.e. one-half the pixel width of CCD 402). In this embodiment, the gap between the top of control device 403 and photocathode 404 is approximately 10 µm. Control device is approximately 30 µm thick. In this configuration, the potential at the top of each hole 410 is substantially −60 V. Notably, holes 410 are formed perpendicular to a surface of photocathode 404, thereby minimizing electrons impacting the sidewalls of holes 410, which in turn minimizes the generation of secondary electrons.

A portion of the control device 403 is shown in more detail from a top view in FIG. 4D(1) and in cross section in FIG. 4D(2). As shown in FIGS. 4D(1) and 4D(2), first electrodes 412 and second electrodes 446 surround each of holes 410 in a control device body 484. The width of first electrodes 412 and second electrodes 446 is much narrower than the width of holes 410 (for example, on the order of at least 1:7). Relatively large gaps 444 exist between the first and second electrodes, for example about 4 µm when the pixel size is approximately 18 µm. In one embodiment, gaps 444 may expose a slightly conductive material. For example, one or more surfaces of body 484 may be doped or implanted, as shown in areas 482 (showing all surfaces). Alternatively, areas 482 may include a thin resistive coating on the surfaces of body 484. In some embodiments, only the surfaces of body 484 between electrodes 412 and 446 may be doped, implanted, or coated. In some embodiments, the surfaces of body 484 may be doped, implanted, or coated prior to deposition of electrodes 412 and 446 so that the slightly conductive surface may extend under some, or all, of electrodes 412 and 446 (as shown in FIG. 4D(2)). Note that similar implementations for the electrodes may be used in the other embodiments shown herein.

Electrodes 412 and 446 are connected to external voltages by conductive traces (not shown) which may be beneath the top surface. In an exemplary embodiment, electrodes 412 and 446 are held at a voltage that is slightly negative relative to the photocathode, for example a voltage of about −65 V when the photocathode is at a potential of about −60V. Because gaps 444 expose a conductive material, an approximately linear voltage gradient will exist between the first and second electrodes. In alternative embodiments, additional electrodes at a different potential may be used between electrodes 412 and 446, thereby allowing a stepwise approximation to the desired voltage gradient to be achieved. In one embodiment, third electrodes 481 may be formed on the bottom surface of control device 403, and may have a potential of −5 V.

Referring back to FIG. 4C, a bottom surface 430 of control device 403 may comprise a surface electrode formed from a conductive material and held at a voltage a few volts negative relative to CCD 402. For example, bottom surface 430 may be held at a voltage of approximately −5 V. In one embodiment, a gap between bottom surface 430 and CCD 202 is approximately 20 µm. One advantage of a small potential difference between bottom surface 430 of control device 403 and CCD 402 is that non-flatness of CCD 402 will have only a minor effect on the electron trajectories and will make little difference to the fraction of electrons emitted in a region of photocathode 404 corresponding to one pixel that arrive at CCD 402 in an adjacent pixel. In one embodiment, the inside surface of holes 410 comprises a conductive material, such as a doped semiconductor or a semi-metallic material. The potential difference between the top and bottom surfaces creates an approximately linear potential gradient along the walls of hole 410 between the top and bottom surfaces.

Line 432 in FIG. 4C represents a −59 V equipotential calculated by solving Laplace's equation for the geometry and voltages described above. Line 434 represents a −4 V equipotential. The other equipotential lines (not labeled) correspond to 5 V intervals between −59 V and −4 V.

FIG. 4E illustrates calculated electron trajectories for the exemplary EBCCD of FIGS. 4C and 4D for electrons leaving photocathode 404 in different directions. Assuming that each electron leaves the photocathode with an energy of approximately 1 eV, lines 451 show the approximate trajectories followed by electrons leaving photocathode 404 near the center of one pixel. Most of the trajectories, e.g. trajectories 451, arrive at CCD 402 using the hole aligned with its corresponding CCD pixel. A few, such as 452, are deflected into an adjacent hole where they will most likely hit the wall as shown. A few (not labeled) land on the top surface. A few (not labeled) turn around and land back on photocathode 402. Because very few of the trajectories shown in FIG. 4E arrive at adjacent pixels of CCD 402, the resolution of this improved EBCCD is (as indicated by the tight distribution) is significantly better than conventional EBCCDs without control device 403. Moreover, because the number of trajectories that terminate on control device 403 or photocathode 404 is a small fraction of the total number of trajectories, the efficiency of this EBCCD is high.

Figure 4F:
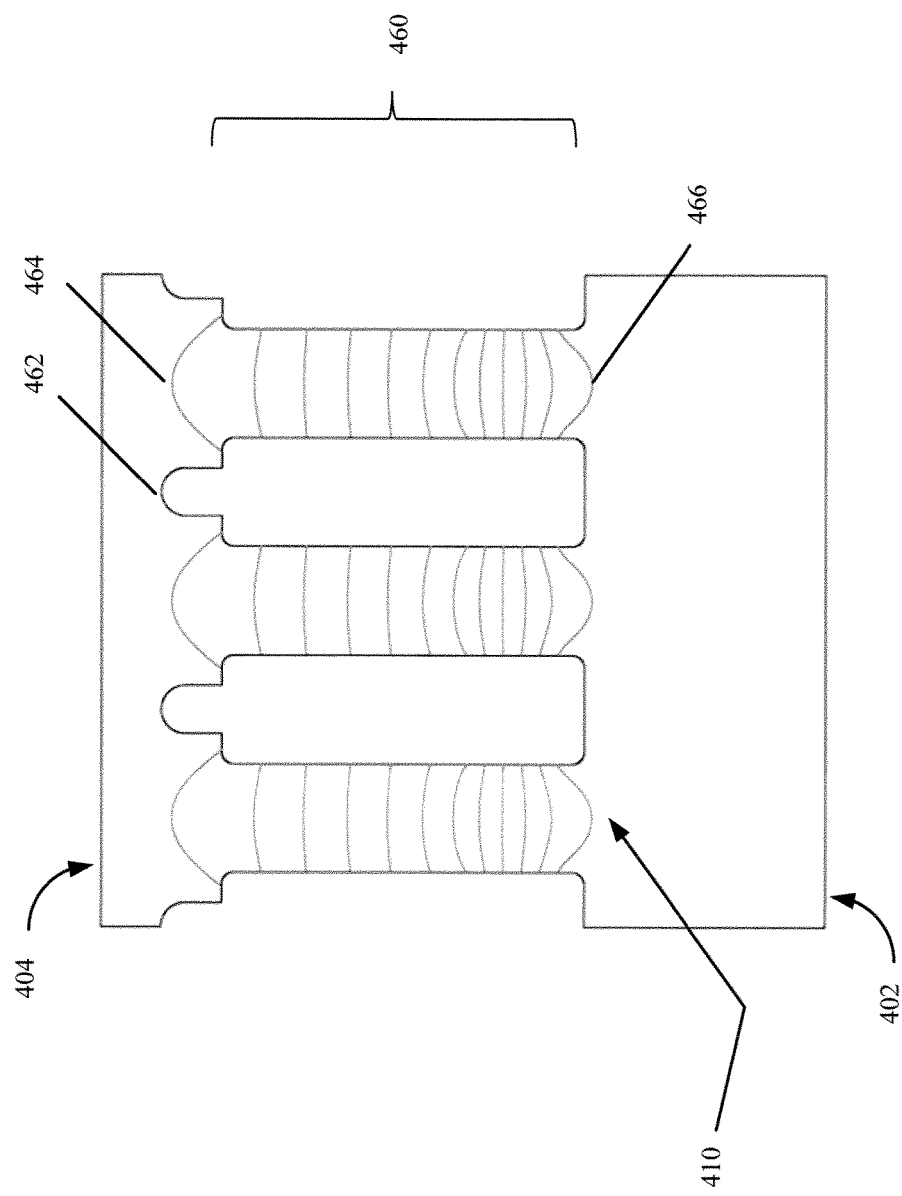
FIG. 4F illustrates a cross-sectional view of three holes of another EBCCD and their exemplary equipotentials.

FIG. 4F shows a cross-sectional view of another exemplary control device 460. In this embodiment, the top surface of control device 460 has a ridge 462 between each hole 410. Apart from this shape difference, the dimensions of this EBCCD can be similar to those described in reference to FIGS. 4C and 4D. The top of ridge 462 may be positioned approximately 5 µm from photocathode 404. Because this distance is small, the potential difference of the top of the ridge relative to the photocathode may be just a few volts, for example approximately −3 V. One advantage of ridge 462 is that the exact voltages are not so critical for reflecting electrons traveling sideways. Specifically, because the top surface of control device 460 is physically located close to photocathode 404, even if the voltage on the surface changes a little, the electric field gradients can be strong enough to reflect the electrons. In this exemplary embodiment, photocathode 404 is held at a voltage of approximately −60V. There is a voltage gradient on the top surface of control device 460 from the center of each ridge at approximately −63 V to approximately −60 V near the edge of each hole 410. The bottom surface of control device 460 is at approximately 0 V, and CCD 402 is at 0 V. Calculated equipotential lines 464 represent approximately the −59 V equipotential, whereas equipotential lines 466 represent approximately −4 V. The other intermediate equipotential lines represent approximately 5 V increments. In a preferred embodiment, the tops of ridges 462 are rounded with a reasonably constant radius of curvature to minimize strong electric field gradients.

Figure 4G:
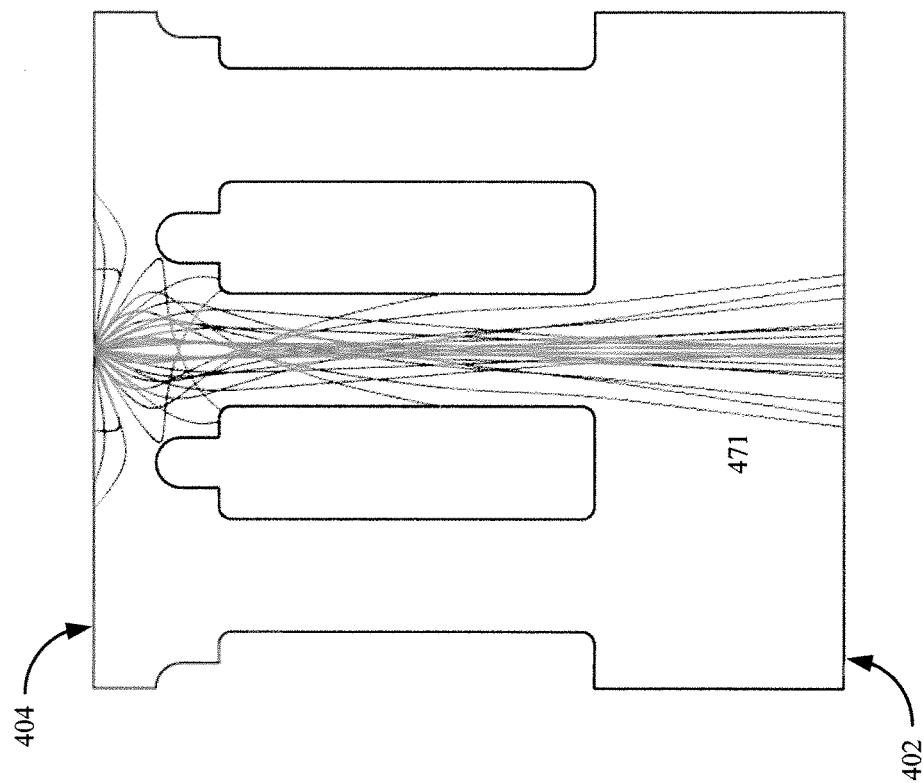
FIG. 4G illustrates calculated electron trajectories for the exemplary EBCCD of FIG. 4F for electrons leaving the photocathode in different directions.

FIG. 4G illustrates shows some calculated electron trajectories for the exemplary embodiment shown in FIG. 4F. Lines 471 show calculated trajectories for electrons emitted from photocathode 404 in different directions with energies of approximately 1 eV. Comparing these trajectories with those of FIG. 4E shows that the control device configuration of FIG. 4F has a more compact distribution of electrons landing on CCD 402, thereby indicating an improved resolution.

Although the above-described embodiments have the photocathode approximately 60 V negative relative to the CCD, it will be appreciated that the focusing effect of the control device largely depends on the voltage differences between the control device and the photocathode. In some embodiments, the photocathode may be at a larger negative voltage such as approximately 500 V or approximately 1000 V, while maintaining voltage differences between the photocathode and the control device to within a few volts or a few tens of volts. In this case, a large potential difference exists between the bottom of the control device and the CCD, which will accelerate the electrons to a high energy before striking the CCD. When a voltage difference of hundreds of volts or more exists between the bottom of the control device and the CCD, then usually a separation of hundreds of microns will be desired between the control device and the CCD. A separation of hundreds of microns can also reduce the effect of non-flatness of the CCD on the performance of the EBCCD. Because the electrons are well-collimated when they leave the control device, small distortions in the electric field from the non-flatness of the CCD are less important than distortions in conventional EBCCDs where the electrons are traveling over a wider range of angles.

As shown above, a wide variety of control device shapes and voltage distributions are possible to ensure improved operating performance of the EBCCD. Thus, the improved EBCCD including the control device is not limited to the control device shapes and voltages described above, but may include other control device shapes and voltage distributions. Although FIGS. 4A through 4G show exemplary embodiments of linear EBCCD detectors, the exemplary configurations can be applied to two-dimensional EBCCD array detectors.

Note that using a silicon MEMS device to implement the control device rather than a metal control device may have some advantages. Specifically, although both embodiments can substantially improve the spatial resolution over conventional EBCCD detectors by collimating the electrons that pass though the array of holes, the metal control device may absorb those electrons with a relatively large horizontal velocity component, thereby reducing the efficiency compared to the EBCCD including the silicon MEMS control device. Because of its electrode structure and the use of appropriate voltages on each electrode, the silicon MEMS control device can direct most of the electrons towards a hole and thus transmit more of the electrons to the CCD.

In some embodiments one, or more, of the control voltages controlling the control device can be adjusted to change the gain of the EBCCD. Although in principle the voltage on the photocathode could be adjusted to change the gain of the EBCCD, the capacitance of the photocathode is large, so high currents would be needed to quickly change the photocathode voltage. By changing voltages on the holes and/or one or more electrodes of the control device, it is possible to reduce the fraction of electrons reaching the CCD and so reduce the effective gain of the EBCCD. In some embodiments this reduction can be done with lower drive currents than needed for changing the photocathode voltage. In some embodiments, active circuits such as transistors, diodes and resistors are fabricated on the MEMS device using standard semiconductor manufacturing techniques. These active circuits can provide local control of electrode voltages and can enable those voltages to be changed more quickly. In some embodiments, such active circuits are used to vary the gain in different sections of the control device so that different regions of the EBCCD have different gains. In some embodiments, individual pixels or groups of pixels can be controlled for gain or for blanking.

In some embodiments, the voltage difference between the lower surface of the control device and the CCD may be small, such as 20 V or less, or substantially zero. With weak, or no, electric field between the bottom of the control device and the CCD, non-flatness of the CCD does not result in significant distortion of the image or significant local variations in gain.

In some embodiments, two cascaded control devices may be used, wherein the first control device is at a voltage potential within ten or a few tens of volts of the potential of the photocathode, and the second downstream control device is at a voltage potential close to that of the CCD, such as less 20 V relative to the CCD. A large potential difference (e.g. tens of volts, hundreds of volts, or even approximately 1000 V) can exist between the first control device. In this configuration, the first control device focuses and collimates the electrons emitted from the photocathode, whereas the second control device accelerates the collimated electrons.

In some embodiments, the alignment between the control device and the CCD may be desired to be done to at least an accuracy of about 20% of the CCD pixel size. In embodiments where the control device and the CCD are both fabricated on silicon, during assembly of the EBCCD, infra-red radiation longer than approximately 1.2 μm in wavelength can be used to detect alignment marks on the two silicon devices (because such radiation can penetrate through silicon). Alignment marks or circuit features on the bottom surface of the CCD (which was actually the top surface of the wafer during manufacturing of the CCD prior to the back-thinning steps) can be aligned with marks on the silicon MEMS control device in order to ensure that both are aligned to the desired accuracy.

The above-described control device can advantageously collimate the electrons, thereby reducing image blur. Because image blur is reduced, less negative voltage is needed on the photocathode in some embodiments. Moreover, the control device can also block most of the ions traveling back from the CCD towards the photocathode, thereby reducing the rate of wear of the photocathode. Additionally, the ions that do reach the photocathode have less energy and ablate less material, thereby prolonging the useful life of the detector. Yet further, the electrons from the control device hit the CCD with lower energy (than without the control device), thereby doing less damage to the CCD. Moreover, these electrons sputter less material from the CCD, thereby resulting in fewer ions and further prolonging the life of the detector.

As described in detail below, wafer, reticle, and photomask inspection systems can advantageously include an EBCCD detector having a control device. Because the scattered light level depends on the roughness of the surface and the size of any particles or defects on that surface, the gain control of the EBCCD having the control device can advantageously be used to compensate for the different light levels.

Figure 5:
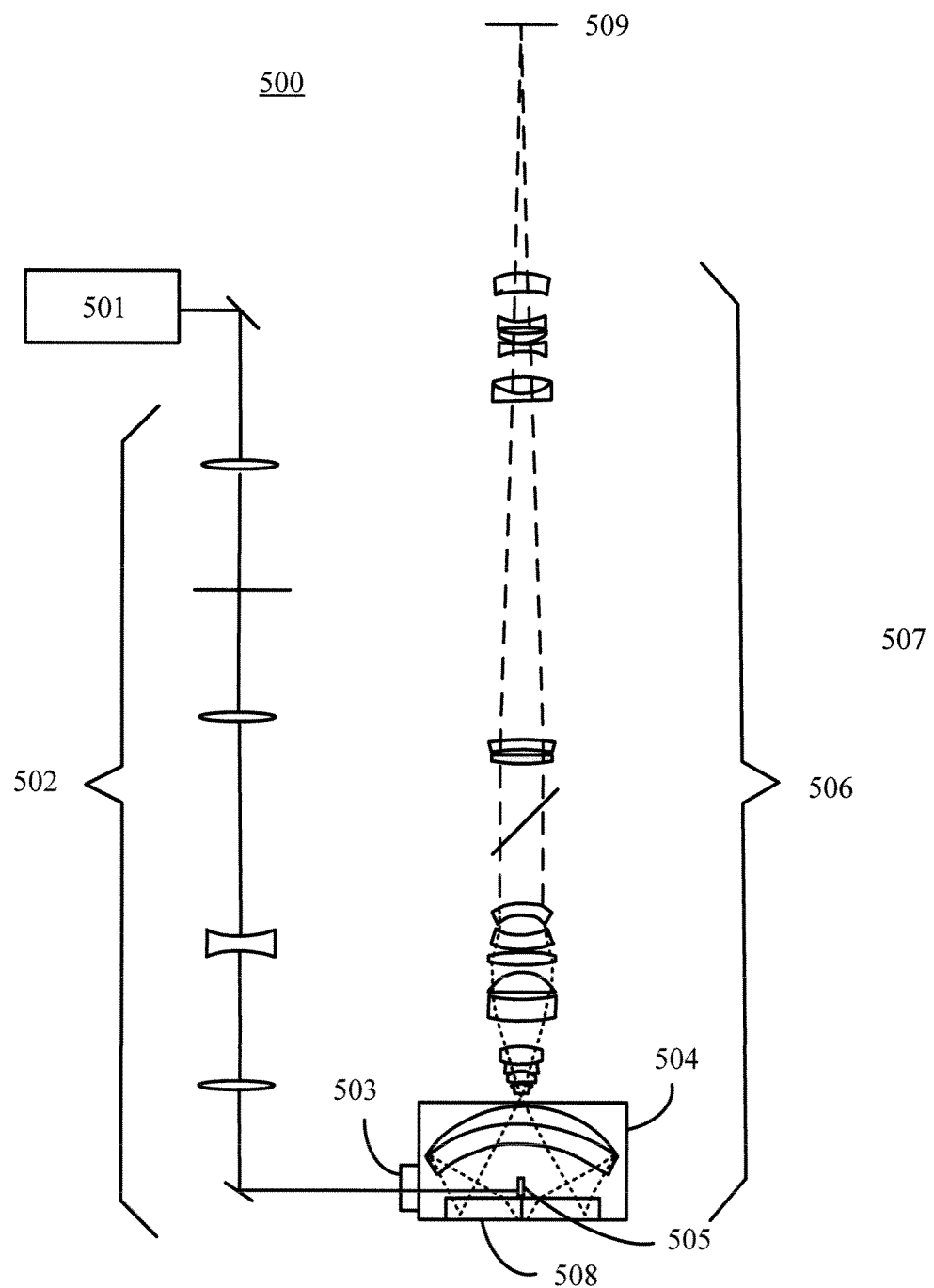
FIG. 5 illustrates the addition of a normal incidence laser dark-field illumination to a catadioptric imaging system.

FIG. 5 illustrates the addition of a normal incidence laser dark-field illumination to a catadioptric imaging system 500. The dark-field illumination includes a UV laser 501, adaptation optics 502 to control the illumination beam size and profile on the surface being inspected, an aperture and window 503 in a mechanical housing 504, and a prism 505 to redirect the laser along the optical axis at normal incidence to the surface of a sample 508. Prism 505 also directs the specular reflection from surface features of sample 508 and reflections from the optical surfaces of an objective lens 506 along the optical path to an image plane (or detector) array 509. Lenses for objective lens 506 can be provided in the general form of a catadioptric objective, a focusing lens group, and a zooming tube lens section. In a preferred embodiment, because the dark-field scattered signal can be weak, image plane (or detector) array 509 can be advantageously implemented by the above-described EBCCD detector having a control device. The EBCCD having the above-described control device is well suited to this application because of its high spatial resolution and, in some embodiments, because of the possibility of controlling its gain in response to, or anticipation of, changes in the scattered light level depending on patterns on the wafer being inspected. U.S. Pat. No. 7,345,825, which issued Mar. 18, 2008 and is incorporated by reference herein, describes certain aspects of system 500 in further detail.

Figure 6A:
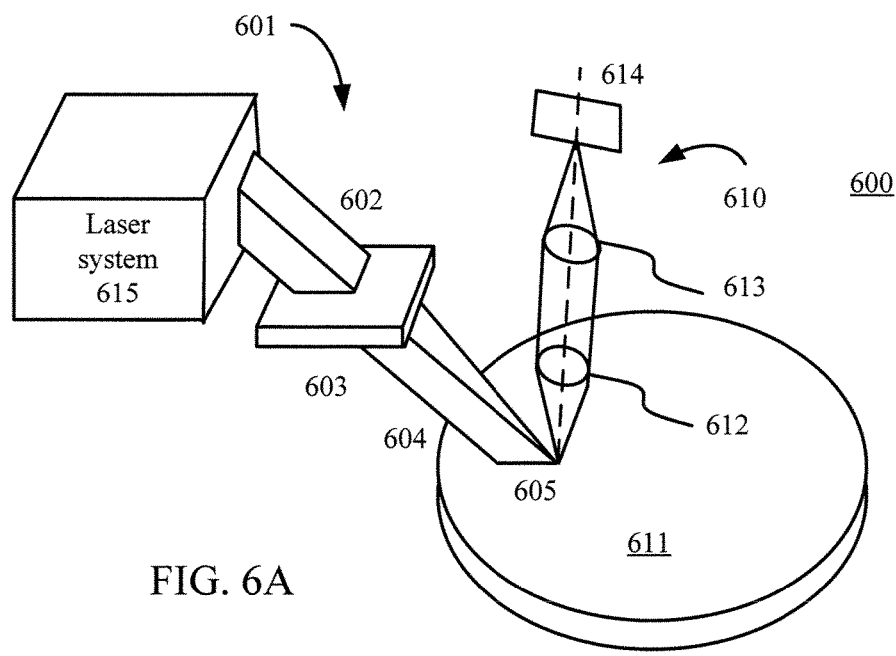
FIGS. 6A and 6B illustrate another surface inspection apparatus that includes an illumination system and a collection system for inspecting areas of a surface.

FIG. 6A illustrates another surface inspection apparatus 600 that includes illumination system 601 and collection system 610 for inspecting areas of surface 611. As shown in FIG. 6A, a laser system 615 is configured to direct light beam 602 through lens 603. Lens 603 is oriented so that its principal plane is substantially parallel to surface 611 and, as a result, illumination line 605 is formed on surface 611 in the focal plane of lens 603. In addition, light beam 602 and focused beam 604 are directed at a non-orthogonal angle of incidence to surface 611. In particular, light beam 602 and focused beam 604 may be directed at an angle between about 1 degree and about 85 degrees from a normal direction to surface 611. In this manner, illumination line 605 is substantially in the plane of incidence of focused beam 604. In some embodiments, illumination line might be approximately 1 or 2, or a few, mm long and 1, 2 or a few μm wide. In some embodiments, instead of a line focus, the illumination may be focused into a series of discrete spots.

Collection system 610 includes lens 612 for collecting light scattered from illumination line 605 and lens 613 for focusing the light coming out of lens 612 onto a device, such as an EBCCD detector 614 including the above-described control device. Dynamic adjustment of the gain of EBCCD detector 614 is important in this kind of inspection system because the scattered and diffracted light levels (and the efficiency of the filters) can vary dramatically from one region of a wafer to another due to the different patterns on the wafer.

Figure 6B:
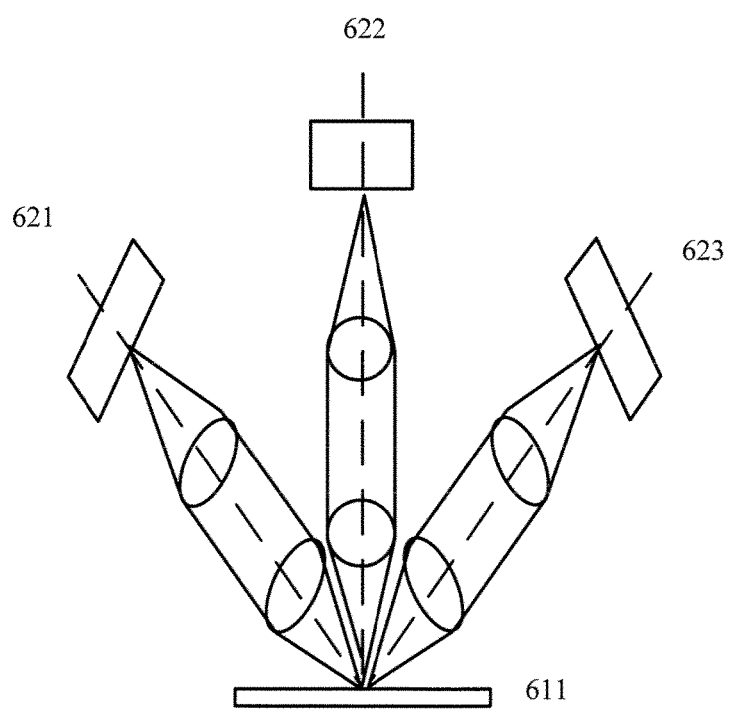

In one embodiment, EBCCD detector 614 may include a linear array of detectors. In such cases, the linear array of detectors within EBCCD detector 614 can be oriented parallel to illumination line 615. In one embodiment, multiple collection systems can be included, wherein each of the collection systems includes similar components, but differ in orientation. For example, FIG. 6B illustrates an exemplary array of collection systems 621, 622, and 623 for a surface inspection apparatus (wherein its illumination system, e.g. similar to that of illumination system 601, is not shown for simplicity). U.S. Pat. No. 7,525,649, which issued on Apr. 8, 2009 and is incorporated by reference herein, describes certain aspects of inspection system 601 in greater detail.

Figure 7:
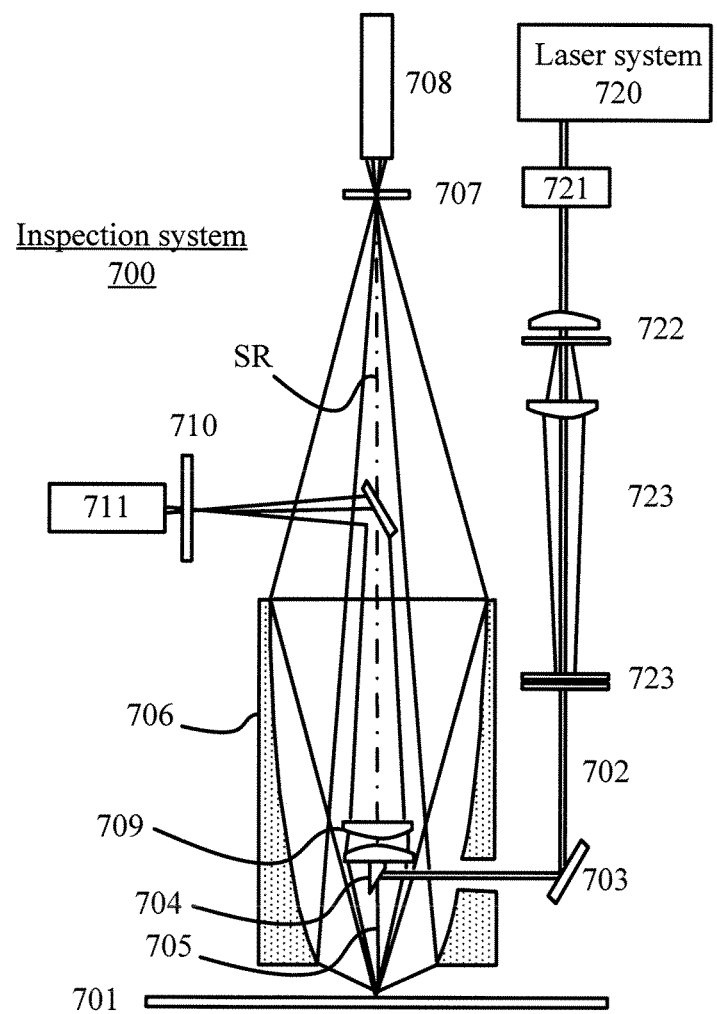
FIG. 7 illustrates the optics of a dark-field unpatterned wafer inspection system.

FIG. 7 illustrates a surface inspection system 700 that can be used for inspecting anomalies on a surface 701. In this embodiment, surface 701 can be illuminated by a substantially stationary illumination device portion of system 700 comprising a laser beam generated by laser system 720. The output of laser system 720 can be consecutively passed through polarizing optics 721, a beam expander and aperture 722, and beam-forming optics 723 to expand and focus the beam.

The focused laser beam 702 is then reflected by a beam folding component 703 and a beam deflector 704 to direct the beam 405 towards surface 701 for illuminating the surface. In the preferred embodiment, beam 705 is substantially normal or perpendicular to surface 701, although in other embodiments beam 705 may be at an oblique angle to surface 701.

In one embodiment, beam 705 is substantially perpendicular or normal to surface 701 and beam deflector 704 reflects the specular reflection of the beam from surface 701 towards beam turning component 703, thereby acting as a shield to prevent the specular reflection from reaching the detectors. The direction of the specular reflection is along line SR, which is normal to surface 701. In one embodiment where beam 405 is normal to surface 701, this line SR coincides with the direction of illuminating beam 705, where this common reference line or direction is referred to herein as the axis of inspection system 700. Where beam 705 is at an oblique angle to surface 701, the direction of specular reflection SR would not coincide with the incoming direction of beam 705; in such instance, the line SR indicating the direction of the surface normal is referred to as the principal axis of the collection portion of inspection system 700.

Light scattered by small particles are collected by mirror 706 and directed towards aperture 707 and detector 708. Light scattered by large particles are collected by lenses 709 and directed towards aperture 710 and detector 711. Note that some large particles will scatter light that is also collected and directed to detector 708, and similarly some small particles will scatter light that is also collected and directed to detector 711, but such light is of relatively low intensity compared to the intensity of scattered light the respective detector is designed to detect. In one embodiment, inspection system can be configured for use in detecting defects on unpatterned wafers. In one embodiment, one or more of detectors 708 and 711 can be implemented by an EBCCD having the above-described control device. U.S. Pat. No. 6,271,916, which issued on Aug. 7, 2001 and is incorporated by reference herein, describes certain aspects of inspection system 700 in greater detail.

Figure 8:
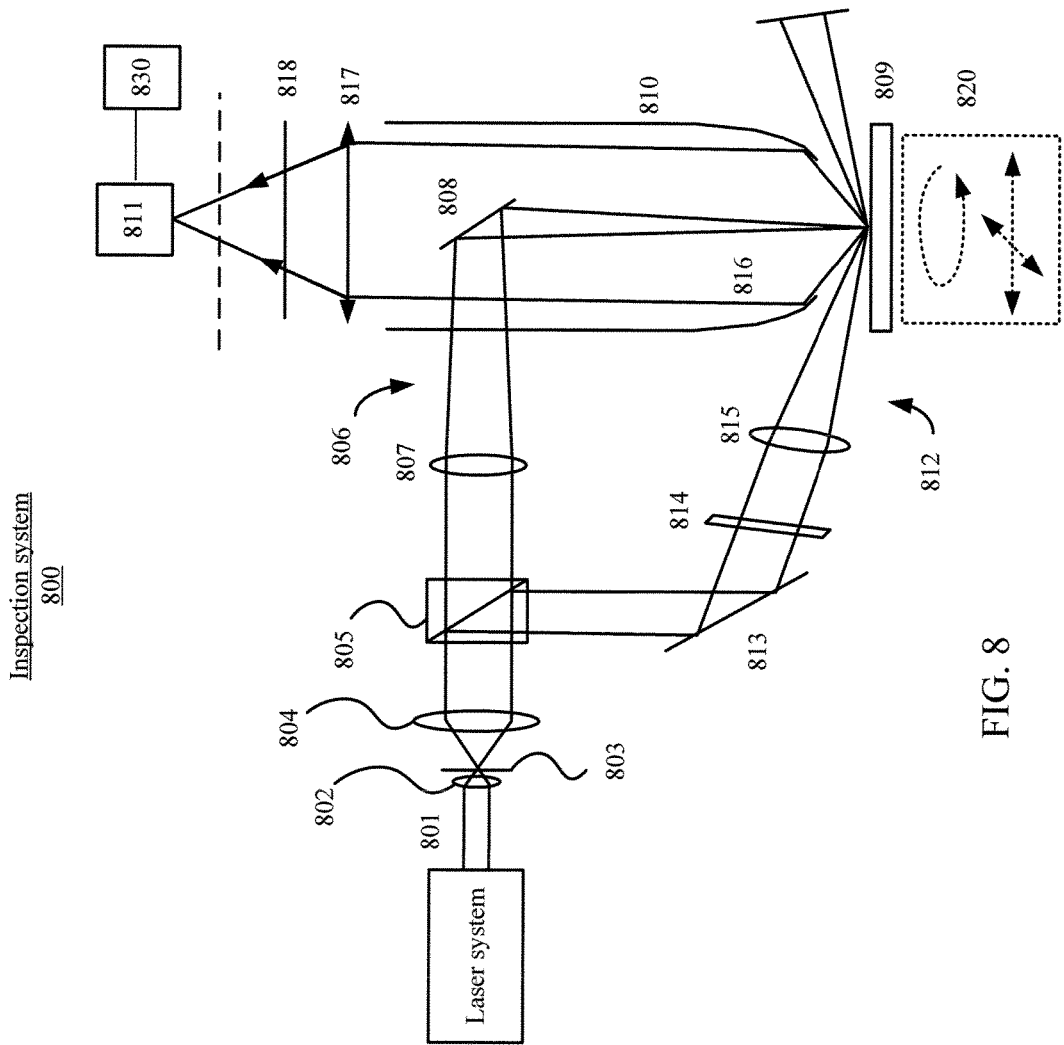
FIG. 8 illustrates a dark-field inspection system configured to implement anomaly detection using both normal and oblique illumination beams.

FIG. 8 illustrates a dark-field inspection system 800 configured to implement anomaly detection using both normal and oblique illumination beams. In this configuration, a laser system can provide a laser beam 801. A lens 802 focuses the beam 801 through a spatial filter 803 and lens 804 collimates the beam and conveys it to a polarizing beam splitter 805. Beam splitter 805 passes a first polarized component to the normal illumination channel and a second polarized component to the oblique illumination channel, where the first and second components are orthogonal. In the normal illumination channel 806, the first polarized component is focused by optics 807 and reflected by mirror 808 towards a surface of a sample 809. The radiation scattered by sample 809 is collected and focused by a paraboloidal mirror 810 to a photomultiplier tube 811.

In the oblique illumination channel 812, the second polarized component is reflected by beam splitter 805 to a mirror 813 which reflects such beam through a half-wave plate 814 and focused by optics 815 to sample 809. Radiation originating from the oblique illumination beam in the oblique channel 812 and scattered by sample 809 is collected by paraboloidal mirror 810 and focused to detector 811. In one embodiment, detector 811 can be implemented by an EBCCD having the above-described control device. The detector and the illuminated spot (from the normal and oblique illumination channels on surface 809) are preferably at the foci of the paraboloidal mirror 810.

Paraboloidal mirror 810 collimates the scattered radiation from sample 809 into a collimated beam 816. Collimated beam 816 is then focused by an objective 817 and through an analyzer 818 to the detector 811. Note that curved mirrored surfaces having shapes other than paraboloidal shapes may also be used. An instrument 820 can provide relative motion between the beams and sample 809 so that spots are scanned across the surface of sample 809. In one embodiment, computer 830 can receive outputs of EBCCD detector 811. U.S. Pat. No. 6,201,601, which issued on Mar. 13, 2001 and is incorporated by reference herein, describes certain aspects of inspection system 800.

Figure 9:
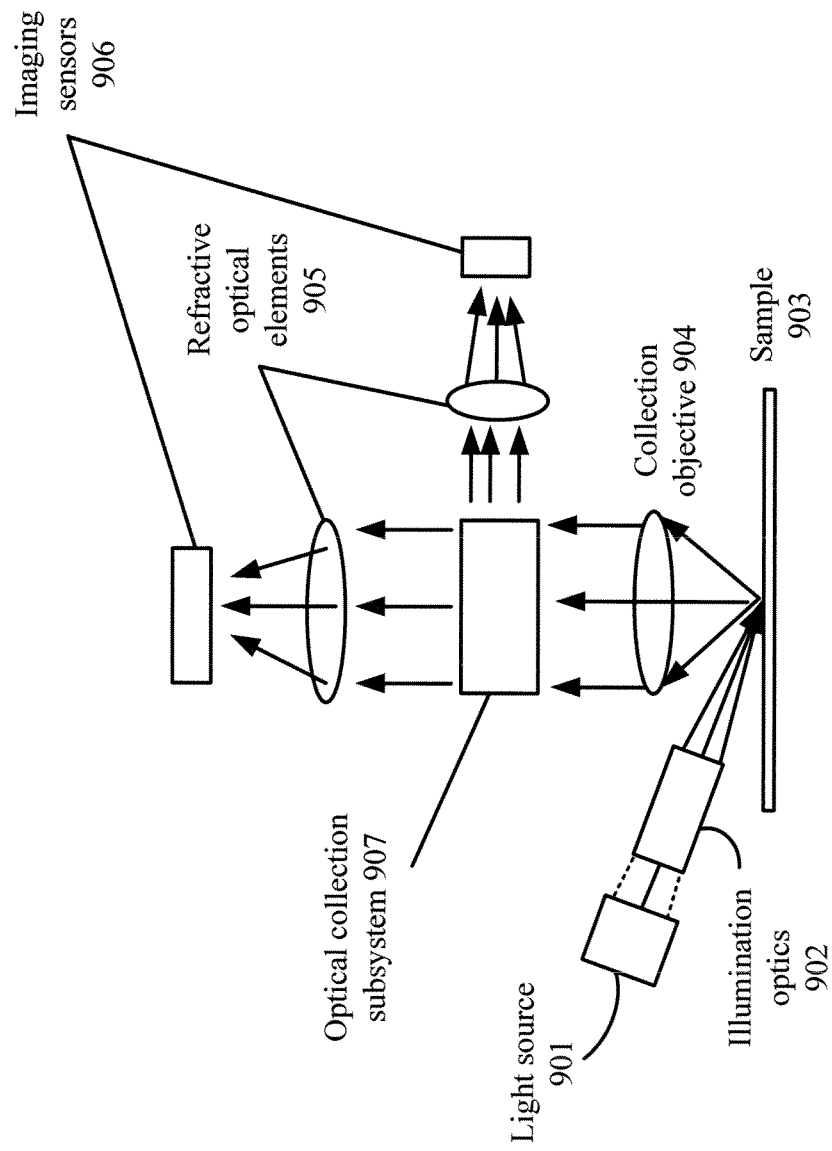
FIG. 9 illustrates another dark-field wafer inspection system including a plurality of EBCCD detectors.

FIG. 9 illustrates another dark-field wafer inspection system 900 including a plurality of EBCCD detectors. In system 900, illumination optics 902 receives the light beam(s) emitted by a light source 901. In one embodiment, illumination optics 902 may include multiple beam splitters and reflective optical elements that provide substantially parallel output light beams to a refractive optical element. That refractive optical element, in turn, can focus the multiple light beams onto a sample 903.

An optical collection subsystem 907 including a scattered light collector and other elements, such as one or more apertures, splitters, polarizing elements, and reflective optical elements, can direct the light scattered from sample onto two image detectors 906. In one embodiment, optical collection subsystem 907 may further include refractive optical elements 905 that are configured to assist the other elements of optical collection subsystem 907 in imaging the scattered light onto image detectors 906. In one embodiment, at least one of image detectors 906 can include the above-described EBCCD detector including a control device. For example, in one embodiment, one detector may be optimized for substantial light scattering while another detector may be optimized for substantially low light scattering. Therefore, during some portions of a scan, the optical element may be configured to direct one portion of the scattered light to one image detector optimized for substantial light scattering and to direct another, different portion of the scattered light to a different image detector that is optimized for low-light scattering. U.S. patent application Ser. No. 13/544,954, filed on Jul. 9, 2012, claiming priority from U.S. Provisional Application 61/506,892 filed on Jul. 12, 2011, describes certain aspects of system 900 in greater detail. Both of these patent applications are incorporated by reference herein.

Figure 10:
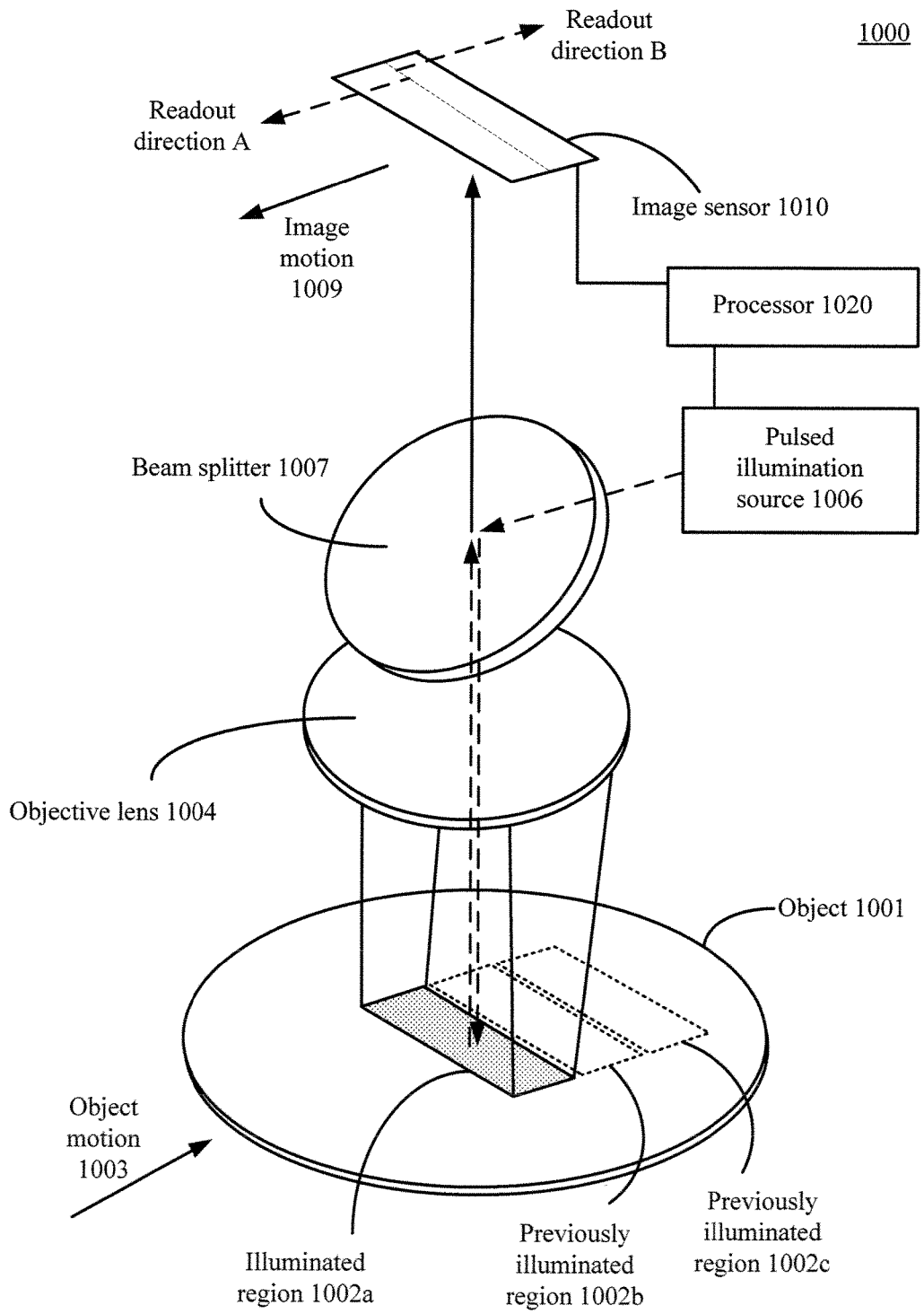
FIG. 10 illustrates an exemplary inspection/metrology system configured to inspect or measure a continuously moving object using a pulsed illumination source.

FIG. 10 illustrates an exemplary inspection/metrology system 1000 configured to use a pulsed illumination source 1006 with a continuously moving object 1001, such as a wafer, mask, or reticle. Advantageously, pulsed illumination 1006 can output a long pulse. Exemplary sources for pulsed illumination 1006 can include a Q-switched laser or a pulsed lamp. A Q-switched laser uses a variable attenuator inside the laser's optical resonator to produce light pulses with extremely high peak power. These light pulses are much higher power than those produced by the same laser operating in continuous mode. A pulsed lamp could be implemented by a deep ultraviolet (DUV) excimer or an extreme ultraviolet (EUV) source. In one preferred embodiment, the pulse duration is close to or somewhat longer than the line period of the time delay integration (TDI) performed.

In system 1000, a beam splitter 1007 would direct illumination pulses from pulsed illumination source 1006 to an objective lens 1004, which would focus that light onto object 1001. Reflected light from object 1001 would then be directed to an image sensor 1010. In one embodiment, image sensor 1010 can be implemented using one of the above-described EBCCD embodiments. Note that other well-known optical components for directing and focusing of the light are not shown for simplicity in FIG. 10. A processor 1020, which is coupled to image sensor 1010, is configured to provide synchronization of illumination pulses from pulsed illumination source 1006 with control and data signals to and from image sensor 1010 as well as analysis of the image data. In the above-described configuration, object 1001 has an object motion 1003 and the image on the image sensor 1010 has an image motion 1009.

In accordance with one aspect of system 1000, because of object motion 1003, the illuminated region will continuously move across object 1001 as indicated by illuminated region 1002a (e.g. time period N), previously illuminated region 1002b (e.g. time period N−1), and previously illuminated region 1002c (e.g. time period N−2). Each of illuminated regions 1002a, 1002b, and 1002c can be a thin rectangular-shaped region (not shown to scale for ease of viewing). Note the regions are shown separated for clarity, but may overlap to provide 100%, imaging coverage, or for additional redundancy and performance during defect detection.

In accordance with another aspect of system 1000, image sensor 1010 can perform a TDI-mode operation during an illumination pulse. During this TDI-mode operation, charges stored by pixels of the image sensor are shifted only in a first direction. System 1000 can also perform a split-readout operation during non-illumination. During this split-readout operation, first charges stored by first pixels of the image sensor are shifted in the first direction and second charges stored by second pixels of the image sensor are concurrently shifted in a second direction, the second direction being opposite to the first direction.

Thus, system 1000 can advantageously combine beneficial properties of TDI readout mode with fast readout capability of pulsed image architectures. Other aspects of system 1000 are described in further detail in U.S. Patent Application 61/735,427, entitled "Method And Apparatus For High Speed Acquisition Of Moving Images Using Pulsed Illumination", filed on Dec. 10, 2012, which is incorporated by reference herein.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. For example, although round holes in the control device are shown in the above embodiments, the holes may be oval or rectangular in other embodiments. In general, the holes are shaped and sized based on the shape and size of the corresponding (and aligned) pixels of the CCD. Having holes with sharp corners may increase electric field gradients, which would be undesirable in applications where the CCD is a two-dimensional pixel array. However, in application where the CCD is a one-dimensional pixel array, then relatively few electrons will impinge on the end pixels. Because the corners will have fewer electrons impinging, the probability of electrons encountering undesirable electric field gradients is minimal. As a result, sharp corners in those embodiments may be acceptable. Also, as indicated above, where the control device is fabricated using semiconductor technology, voltage control devices and/or detection devices may be formed in the control device. In some embodiment, to ensure minimal impact on the electron trajectory, these devices may instead be formed on the bottom of the control device (i.e. facing the CCD). In some embodiments, the electron detector may comprise a CMOS image sensor rather than a CCD. Accordingly, it is intended that the scope of the invention be defined by the following claims and their equivalents.

The invention claimed is:

1. An electron-bombarded charge-coupled device (EBCCD) comprising:

an assembly including a window;
a photocathode inside the assembly and adjacent to the window;
a CCD device inside the assembly and positioned to collect electrons emitted from the photocathode; and
a control device positioned between the photocathode and the CCD, the control device comprising a silicon wafer having a plurality of holes passing through the silicon wafer, wherein the plurality of holes are formed perpendicular to a surface of the photocathode such that minimal impact of said electrons traveling perpendicularly to the CCD occurs on sidewalls of said plurality of holes, and wherein a pattern of the plurality of holes is aligned with a pattern of pixels in the CCD such that each said hole of the plurality of holes is aligned with only one corresponding pixel of the pattern of pixels, whereby most electrons passing through said each hole of the plurality of holes land on said corresponding pixel of said pattern of pixels, each hole being surrounded by at least one first electrode formed on a surface of the silicon wafer facing the photocathode.

2. The EBCCD of claim 1, wherein the CCD has a boron coating on its surface facing the at least one first electrode.

3. The EBCCD of claim 1, wherein the CCD comprises a back-thinned CCD.

4. The EBCCD of claim 1, wherein the CCD comprises a time-delay integration CCD.

5. The EBCCD of claim 1, wherein an exterior surface of the window includes an anti-reflective coating.

6. The EBCCD of claim 1, wherein the control device further comprises a plurality of ridges between the plurality of holes.

7. The EBCCD of claim 1, wherein the control device is positioned to be separated from the photocathode by approximately half a shorter dimension of a CCD pixel or less.

8. The EBCCD of claim 1, wherein the at least one first electrode includes a plurality of first electrodes, each first electrode surrounding a given hole and separated from the given hole by a gap.

9. The EBCCD of claim 1, wherein the at least one first electrode includes a plurality of ring electrodes and one surface electrode, each of the plurality of ring electrodes separated from a given hole by a first gap, and separated from the surface electrode by a second gap.

10. The EBCCD of claim 8, further including at least one second electrode surrounding the holes of the control device and positioned on a surface of the control device facing the CCD.

11. A method of operating an electron-bombarded charge-coupled device (EBCCD), the method comprising:
holding a photocathode of the EBCCD at a negative voltage relative to a CCD of the EBCCD; and
focusing electrons traveling from the photocathode towards pixels of the CCD by causing the electrons to pass through a plurality of holes defined in a control device disposed between the photocathode and the CCD, wherein the plurality of holes are formed perpendicular to a surface of the photocathode such that minimal impact of said electrons traveling perpendicularly to the CCD occurs on sidewalls of said plurality of holes,
wherein the control device comprises a silicon wafer processed using photolithography such that the plurality of holes are etched therethrough and arranged in a pattern corresponding to a plurality of pixels on the CCD, and
wherein focusing electrons further comprises aligning each hole of the plurality of holes of the control device with only one corresponding pixel of the plurality of pixels on the CCD such that most electrons passing through said each hole land on said corresponding pixel.

12. The method of claim 11, further including holding inside surfaces of the holes of the control device at a positive voltage relative to the photocathode.

13. The method of claim 12, further including holding a first electrode surrounding at least one hole at a different voltage than the inside surfaces of the holes, the first electrode positioned on a surface of the control device facing the photocathode.

14. The method of claim 13, wherein the first electrode is held at a negative voltage relative to the inside surfaces of the holes.

15. The method of claim 14, further including holding a second electrode at a different potential from the first electrode, the second electrode surrounding at least one hole of the control device and positioned to face the CCD.

16. The method of claim 12, further including holding some regions of a surface of the control device closest to the photocathode at a potential similar to that of the photocathode or slightly negative relative to the photocathode.

17. A dark-field inspection system comprising:
optics for directing light to a sample being inspected;
optics for collecting scattered light from the sample and directing collected light; and
an electron-bombarded charge-coupled device (EBCCD) detector for receiving the collected light, the EBCCD detector comprising:
an assembly including a window;
a photocathode inside the assembly and adjacent to the window;
a CCD device inside the assembly and positioned to collect electrons emitted from the photocathode; and
a control device positioned between the photocathode and the CCD, the control device comprising a silicon wafer having a plurality of holes passing through the silicon wafer, wherein the plurality of through holes are formed perpendicular to a surface of the photocathode such that minimal impact of said electrons traveling perpendicularly to the CCD occurs on sidewalls of said plurality of holes, and wherein a pattern of the plurality of through holes is aligned with a pattern of pixels in the CCD such that each said through hole of the plurality of through holes is aligned with only one corresponding pixel of the pattern of pixels, whereby most electrons passing through each said through hole of the plurality of through holes land on said corresponding pixel of said pattern of pixels, each hole being surrounded by at least one first electrode formed on a surface of the silicon wafer facing the photocathode.

18. The dark-field inspection system of claim 17, wherein the CCD is a time-delay integration CCD.

19. The dark-field inspection system of claim 18, wherein the time-delay integration CCD comprises multiple readout registers are readable in parallel.

20. A method of inspecting a semiconductor wafer, the method comprising:
illuminating a region of the wafer with light;
collecting scattered light from the wafer; and
directing collected light to an electron-bombarded charge-coupled device (EBCCD) detector, wherein the EBCCD detector performs a process comprising:

holding a photocathode of the EBCCD at a negative voltage relative to a CCD of the EBCCD, said CCD including a plurality of pixels arranged in a pattern; and focusing electrons traveling from the photocathode towards pixels of the CCD by causing the electrons to pass through a plurality of holes defined in a control device disposed between the photocathode and the CCD such that minimal impact of said electrons traveling perpendicularly to the CCD occurs on sidewalls of said plurality of holes, wherein the control device comprises a silicon wafer processed using photolithography such that the plurality of holes are etched therethrough and arranged in the pattern of the plurality of pixels, and wherein the control device is positioned such that each said hole of the plurality of holes is aligned with only one corresponding pixel of the pattern of pixels, whereby most electrons passing through said each hole of the plurality of holes land on said corresponding pixel of said pattern of pixels.

21. The inspection method of claim 20, wherein the CCD performs time-delay integration.

22. The inspection method of claim 21 wherein the tine-delay integration uses multiple registers read out in parallel.

23. An inspection system comprising:
a pulsed illumination source;
an image sensor including an electron-bombarded charge-coupled device (EBCCD) detector, the EBCCD detector comprising:
an assembly including a window;
a photocathode inside the assembly and adjacent to the window;
a CCD inside the assembly and positioned to collect electrons emitted from the photocathode; and
a control device positioned between the photocathode and the CCD, the control device comprising a silicon wafer having a plurality of holes passing therethrough, wherein the plurality of holes are formed perpendicular to a surface of the photocathode such that minimal impact of said electrons traveling perpendicularly to the CCD occurs on sidewalls of said plurality of holes, and wherein a pattern of the plurality of holes is aligned with a pattern of pixels in the CCD such that each said hole of the plurality of holes is aligned with only one corresponding pixel of the pattern of pixels, whereby most electrons passing between the photoelectron and the CCD through each said hole of the plurality of holes land on said corresponding pixel of said pattern of pixels, each hole being surrounded by at least one first electrode formed on a surface of the silicon wafer facing the photocathode;
optical components configured to direct pulsed illumination from the pulsed illumination source to a continuously moving object, and direct reflected light from the object to the image sensor; and
a processor configured to operate the image sensor, a configuration performing a process comprising:
performing a timed delay integration (TDI) operation during an illumination pulse, wherein charges stored by pixels of the image sensor are shifted only in a first direction during TDI operation; and
performing a split-readout operation during non-illumination, wherein first charges stored by first pixels of the image sensor are shifted in the first direction and second charges stored by second pixels of the image sensor are concurrently shifted in a second direction during the split-readout operation, the second direction being opposite to the first direction.

* * * * *